United States Patent
Rigatti et al.

(10) Patent No.: US 12,319,962 B2
(45) Date of Patent: *Jun. 3, 2025

(54) METHODS FOR SEQUENCING POLYNUCLEOTIDES

(71) Applicant: Illumina Cambridge Limited, Cambridge (GB)

(72) Inventors: Roberto Rigatti, Cambridge (GB); Niall Anthony Gormley, Cambridge (GB); Jonathan Mark Boutell, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 514 days.

This patent is subject to a terminal disclaimer.

(21) Appl. No.: 17/689,237

(22) Filed: Mar. 8, 2022

(65) Prior Publication Data

US 2022/0259651 A1 Aug. 18, 2022

Related U.S. Application Data

(63) Continuation of application No. 16/436,525, filed on Jun. 10, 2019, now Pat. No. 11,279,975, which is a (Continued)

(51) Int. Cl.
    *C12P 19/34* (2006.01)
    *C12Q 1/6874* (2018.01)

(52) U.S. Cl.
    CPC .................. *C12Q 1/6874* (2013.01)

(58) Field of Classification Search
    USPC .......... 435/6.1, 6.11, 6.12, 91.1, 91.2, 91.51, 435/287.1; 436/94, 501; 536/23.1, 24.3,
    (Continued)

(56) References Cited

U.S. PATENT DOCUMENTS

| | | |
|---|---|---|
| 5,302,509 A | 4/1994 | Cheeseman |
| 5,641,658 A | 6/1997 | Adams et al. |

(Continued)

FOREIGN PATENT DOCUMENTS

| | | |
|---|---|---|
| WO | WO199106678 | 5/1991 |
| WO | WO199844151 | 10/1998 |

(Continued)

OTHER PUBLICATIONS

Batzoglou et al., "ARACHNE: a whole-genome shotgun assembler", Genome Research, 12(1), 2002, 177-189.

(Continued)

*Primary Examiner* — Frank W Lu
(74) *Attorney, Agent, or Firm* — Illumina Cambridge Limited

(57) ABSTRACT

Provided herein is a method for sequencing a polynucleotide molecules. The method includes the steps of providing a plurality of polynucleotide molecules attached to a surface, wherein a first portion of each polynucleotide molecule is attached to a first location of the surface and a second portion of each polynucleotide molecule is attached to a second location of the surface, the relative proximity of the first and second locations being correlated with the probability that the first and second portions are paired, separating the first and second portions of the polynucleotide molecules on the surface, determining the sequences of the first and second portions of the polynucleotide molecules and comparing the relative proximities and the sequences to determine which first and second portions are paired and to determine the sequence of the target polynucleotide molecules.

14 Claims, 15 Drawing Sheets

Related U.S. Application Data continuation of application No. 14/683,580, filed on Apr. 10, 2015, now Pat. No. 10,329,613, which is a continuation of application No. 13/219,422, filed on Aug. 26, 2011, now Pat. No. 9,029,103.

(60) Provisional application No. 61/377,732, filed on Aug. 27, 2010.

(58) Field of Classification Search
USPC .................................................. 536/24.33
See application file for complete search history.

(56) References Cited

U.S. PATENT DOCUMENTS

| | | |
|---|---|---|
| 5,754,291 A | 5/1998 | Kain |
| 5,981,956 A | 11/1999 | Stern |
| 6,060,288 A | 5/2000 | Adams et al. |
| 6,090,592 A | 7/2000 | Adams et al. |
| 6,172,218 B1 | 1/2001 | Brenner |
| 6,210,891 B1 | 4/2001 | Nyren et al. |
| 6,258,568 B1 | 7/2001 | Nyren |
| 6,274,320 B1 | 8/2001 | Rothberg et al. |
| 6,306,597 B1 | 10/2001 | Macevicz |
| 6,468,751 B1 | 10/2002 | Adams et al. |
| 6,664,079 B2 | 12/2003 | Ju et al. |
| 6,969,488 B2 | 11/2005 | Bridgham et al. |
| 7,057,026 B2 | 6/2006 | Barnes et al. |
| 7,115,400 B1 | 10/2006 | Adessi et al. |
| 7,329,860 B2 | 2/2008 | Feng et al. |
| 7,414,116 B2 | 8/2008 | Milton et al. |
| 7,427,673 B2 | 9/2008 | Balasubramanian et al. |
| 7,541,444 B2 | 6/2009 | Milton et al. |
| 7,544,794 B1 | 6/2009 | Benner |
| 7,790,418 B2 | 9/2010 | Mayer |
| 9,029,103 B2 | 5/2015 | Rigatti et al. |
| 10,329,613 B2 * | 6/2019 | Rigatti .................. C12Q 1/6874 |
| 11,279,975 B2 * | 3/2022 | Rigatti .................. C12Q 1/6874 |
| 2003/0022231 A1 | 1/2003 | Wangh et al. |
| 2005/0059048 A1 | 3/2005 | Gunderson et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0110638 A1 | 5/2007 | Heiner et al. |
| 2007/0128624 A1 | 6/2007 | Gormley et al. |
| 2007/0166705 A1 | 7/2007 | Milton et al. |
| 2007/0238101 A1 | 10/2007 | Ruan et al. |
| 2009/0088327 A1 | 4/2009 | Rigatti et al. |
| 2009/0118128 A1 | 5/2009 | Liu et al. |
| 2009/0181370 A1 | 7/2009 | Smith et al. |
| 2009/0191598 A1 | 7/2009 | Ruan et al. |
| 2009/0226975 A1 | 9/2009 | Sabot et al. |
| 2010/0022412 A1 | 1/2010 | Rigatti et al. |
| 2014/0220587 A1 | 8/2014 | Green, Jr. et al. |

FOREIGN PATENT DOCUMENTS

| | | |
|---|---|---|
| WO | WO199844152 | 10/1998 |
| WO | WO 2002046456 | 6/2002 |
| WO | WO 2004018497 | 3/2004 |
| WO | WO 2005065814 | 7/2005 |
| WO | WO 2006064199 | 6/2006 |
| WO | WO 2007010251 | 1/2007 |
| WO | WO 2007010252 | 1/2007 |
| WO | WO 2007010254 | 1/2007 |
| WO | WO 2007010263 | 1/2007 |
| WO | WO 2007123744 | 1/2007 |
| WO | WO 2007060456 | 5/2007 |
| WO | WO 2007091077 | 8/2007 |
| WO | WO 2007107710 | 9/2007 |
| WO | WO 2008007951 | 1/2008 |
| WO | WO 2008041002 | 4/2008 |
| WO | WO 2009032167 | 3/2009 |
| WO | WO 2010038042 | 4/2010 |
| WO | WO 2011025477 | 3/2011 |
| WO | WO 2011137368 | 3/2011 |
| WO | WO 2011074960 | 6/2011 |
| WO | WO 2012106546 | 8/2012 |
| WO | WO 2014108810 | 7/2014 |
| WO | WO 2015095226 | 6/2015 |

OTHER PUBLICATIONS

Bentley et al., "Accurate whole human genome sequencing using reversible terminator chemistry", Nature, vol. 456, 2008, 53-59.

European Search Report and Written Opinion, EP17161616, mailed Jul. 14, 2017, Jul. 14, 2017, 15 pages.

Fullwood et al., "Chromatin interaction analysis using paired-end tag sequencing", Current Protocols in Molecular Biology, Supplement 89, Jan. 21, 2010, 21.15.1-21.15.25.

Fullwood et al., "Next-generation DNA sequencing of paired-end tags (PET) for transcriptome and genome analyses", Genome Research, vol. 19, No. 4, Apr. 1, 2009, 521-532.

Hiatt et al., "Parallel, tag-directed assembly of locally derived short sequence reads", Nature Methods, Vo. 7, No. 2, ISSN: 1548-7091; XP055005905, Jan. 17, 2010, 119-122.

Holt et al., "The new paradigm of flow cell sequencing", Genome Research, vol. 18, No. 6, Jun. 2008, 839-846.

Ronaghi et al., "A Sequencing Method Based on Real-Time Pyrophosphate", Science 281 (5375), Jul. 17, 1998, 363-365.

Ronaghi, "Pyrosequencing sheds light on DNA sequencing", Genome Res, 11(1), 2001, 3-11.

Ronaghi, et al., "Real-time DNA sequencing using detection of Pyrophosphate release" *Analytical Biochemistry* 242 (1), 84-9 (1996).

Wilhelm et al., "RNA-Seq-quantitative measurement of expression through massively parallel RNA-sequencing", A Companion to Methods in Enzymology, vol. 48, No. 3, Jul. 1, 2009, 249-257.

* cited by examiner

1. Library construction

2. Hybridize to P5-SBS3 oligos inside the flowcell

3. Perform extension in the presence of modified nucleotide (i.e. uracil)

4. Cleave modified nucleotide to generate 3' phosphate

5. Block P5-SBS3 oligonucleotides that did not participate in hybridization and extension 6. Cleave 3' phosphate 7. Ligate P7'-SBS8' adapter 8. Deprotect P5 and P7 oligonucleotides 1. Library construction 2. Hybridize to solid surface grafted with P5 oligos 3. Use P5 oligos on the surface as sequencing primers to sequence the two ends of the DNA fragments 1. Library construction 2. Ligate 5' end of fragment onto oligos on the surface = P5.  ✷ = cleavable nucleotide (i.e. uracil or 8oxoG)

3. P5' sequence at the 3' end of the insert hybridizes to P5 on the surface

4. Extend off P5 on the surface to form dsDNA molecule

5. Cleave P5 oligos at cleavable and deprotect 3' phosphates with PNK

6. Sequence the ends using surface-bound P5 oligos as sequencing primers

1. Library construction

2. Hybridize to solid surface grafted with P5 oligos

3. Extend P5 oligos

1. Library construction

2. Hybridize to solid surface grafted with P5 oligos

3. Insert transposons

1. Construct library by fragmentation and ligation of two different 3' adapters (i.e. P5 and P6)

2. Prepare solid substrate (patterned surface containing two types of patches). Each patch will contain two types of primers. One patch will have P5 and P7 whereas the other patch will contain P6 and P7 primers

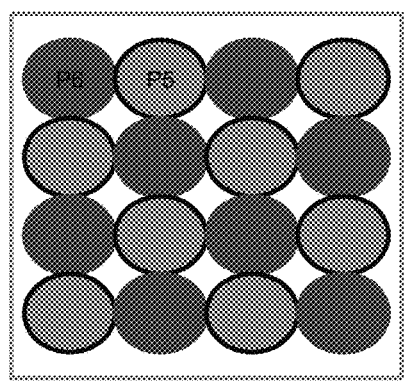

3. Seed library (one end will hybridise to a P5 patch whereas the other end will hybridise to a P6 patch)

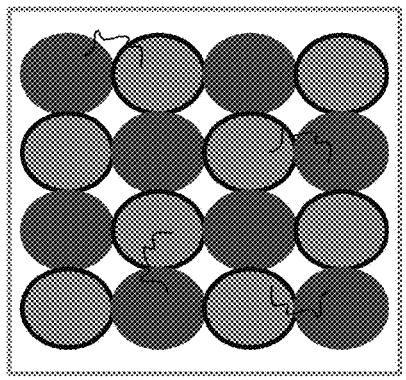

Fig. 6A

4. Perform extension with dNTPs and DNA polymerase

P5 P7          P6 P7

5. Insert transposons (P7' sequences)

P5 P7          P6 P7

6. Clonal amplification-linearisation of P5 and P6 oligos-hybridisation of sequencing primer

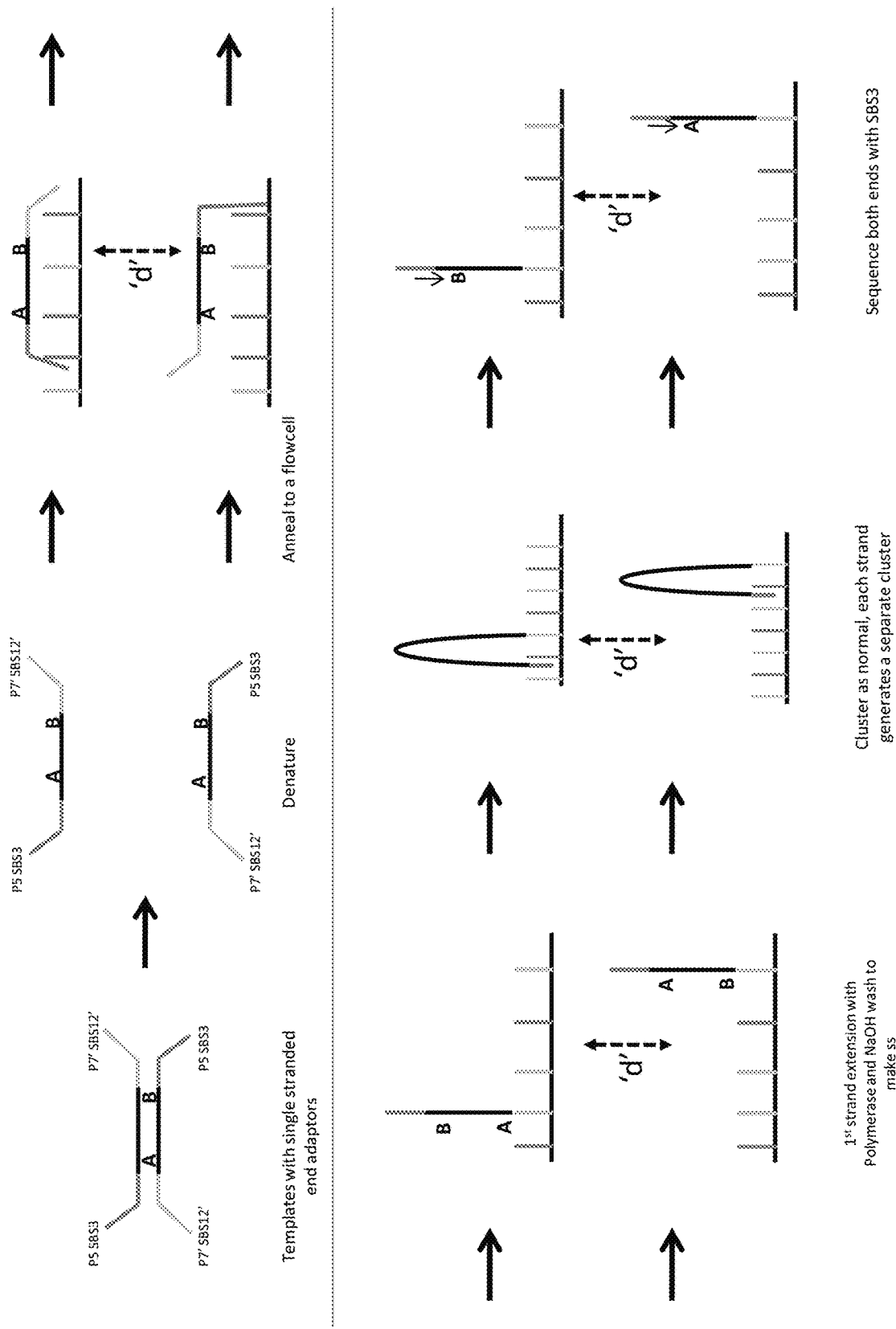

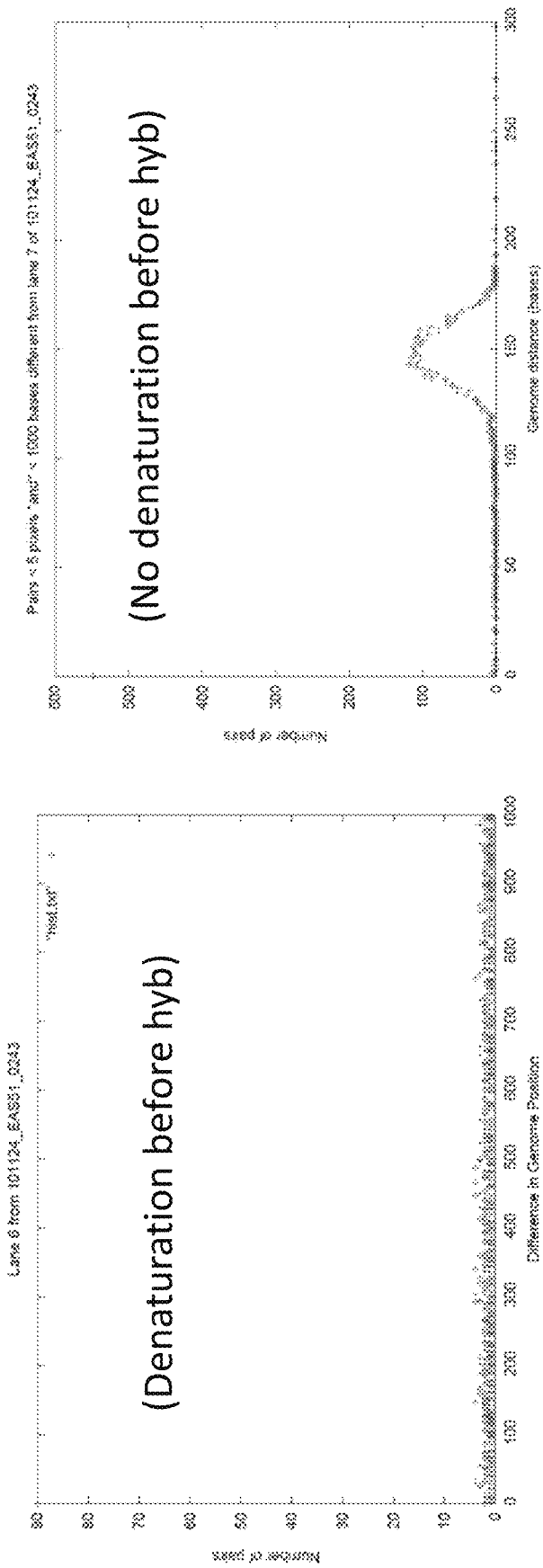

METHODS FOR SEQUENCING POLYNUCLEOTIDES

CROSS-REFERENCE TO RELATED APPLICATIONS

This application is a continuation of U.S. application Ser. No. 16/436,525 filed Jun. 10, 2019, now U.S. Pat. No. 11,279,975 which is a continuation of U.S. application Ser. No. 14/683,580, filed on Apr. 10, 2015, now U.S. Pat. No. 10,329,613, which is a continuation of U.S. application Ser. No. 13/219,422, filed on Aug. 26, 2011, now U.S. Pat. No. 9,029,103, which claims priority to U.S. Prov. App. No. 61/377,732, filed Aug. 27, 2010, which are each incorporated by reference herein in its entirety.

BACKGROUND

The technique of paired-end (PE) or pairwise sequencing is generally known. Paired-end sequencing allows the determination of two or more reads of sequence from two places on a single polynucleotide duplex. The advantage of the paired-end approach is that there is significantly more information to be gained from sequencing two stretches from a single template than from sequencing each of two independent templates in a random fashion. With the use of appropriate software tools for the assembly of sequence information it is possible to make use of the knowledge that the paired-end sequences are not completely random, but are known to occur on a single duplex, and are therefore linked or paired in the genome. This information has been shown to greatly aid the assembly of whole genome sequences into a consensus sequence.

SUMMARY

Provided herein is a method for sequencing a plurality of polynucleotide molecules. The method includes the steps of providing a plurality of polynucleotide molecules attached to a surface, wherein a first portion of each polynucleotide molecule is attached to a first location of the surface and a second portion of each polynucleotide molecule is attached to a second location of the surface, the relative proximity of the first and second locations being correlated with the probability that the first and second portions are paired, separating the first and second portions of the polynucleotide molecules on the surface, determining the sequences of the first and second portions of the polynucleotide molecules, and comparing the relative proximities and the sequences to determine which first and second portions are paired and to determine the sequence of the target polynucleotide molecules.

Also provided is a method of sequencing including the steps of providing a plurality of polynucleotide molecules, each polynucleotide molecule comprising a first and second portion of the target polynucleotide molecule, whereby the first and second portions are paired, attaching the plurality of polynucleotide molecules to a surface, wherein the first portion of each polynucleotide molecule is attached to a first location of the surface and the second portion of each polynucleotide molecule is attached to a second location of the surface, the relative proximity of the first and second locations being correlated with the probability that the first and second portions are paired, separating the first and second portions of the polynucleotide molecules on the surface, determining the sequences of the first and second portions of the polynucleotide molecules, comparing the relative proximities of the first portions and the second portions to determine which first and second portions are paired, and using sequences of the paired first and second portions to determine the sequence of the plurality of target polynucleotide molecules.

The details of one or more embodiments are set forth in the accompanying drawings and the description below. Other features, objects, and advantages will be apparent from the description and drawings, and from the claims.

DESCRIPTION OF DRAWINGS

FIG. 6A is a schematic showing another exemplary sequencing method provided herein using a patterned surface. In (1) genomic DNA is fragmented into double stranded fragments followed by ligation of two different adaptors onto the 3' ends of the fragments, in this example a P5' adaptor on one end and a P6' adaptor on the other end. In (2), a patterned solid surface containing two types of patches is provided, one type of patch containing immobilized P5 and P7 oligos ("a P5 patch") and the other type of patch containing immobilized P6 and P7 oligos ("a P6 patch"). The 3' ends of the fragments are hybridized such that one end of the fragment will hybridize to a P5 patch and a P6 patch.

FIG. 8 is a schematic showing a sequencing method wherein the double stranded fragments containing portions A and B are separated before hybridization to a solid surface. In this schematic each strand will generate a separate cluster. The distance separating the clusters is denoted by 'd.' However, in this case, 'd' will be completely random and will not be correlated to the length of the double stranded fragment.

FIG. 9A is a graph showing the sequencing of an *E. coli* library with an average fragment size of 150 base pairs. According to the schematic shown in FIG. 7, there should be a correlation between the length of the fragment and the distance separating paired clusters of portions A and B. FIG. 9A shows that, when the double stranded fragments are separated prior to hybridization to the surface, the distance between pairs of clusters is random.

FIG. 9B is a graph showing the sequencing of an *E. coli* library with an average fragment size of 150 base pairs. In contrast, FIG. 9B shows that, when portions A and B are separated after the double stranded fragments are hybridized to the surface, the distance between paired clusters of portions A and B is non-random and corresponds to the size of the double stranded fragments.

DETAILED DESCRIPTION

Figure 1:
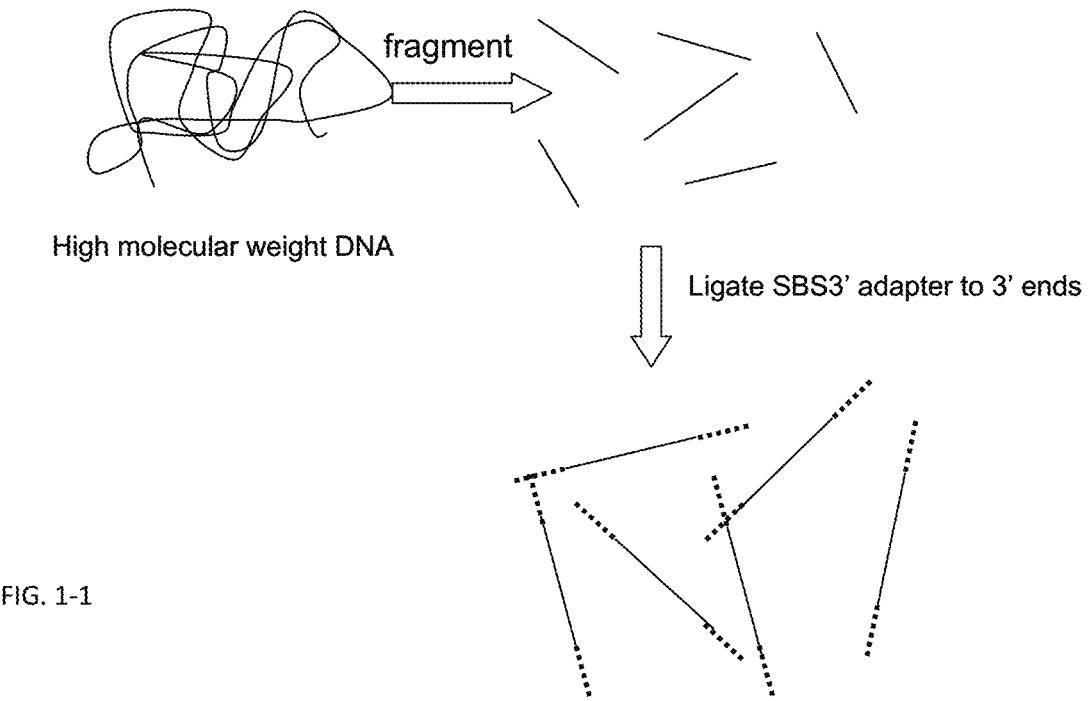
FIG. 1A is a schematic showing an exemplary method described herein using double stranded templates. In (1), genomic DNA is fragmented into double-stranded fragments followed by ligation of SBS3' adapters onto the 3' ends of the fragments. In (2), each 3' end of the ligated fragments is attached to a solid surface by hybridizing to an unblocked P5-SBS3 oligo. The solid surface also contains blocked P5 and blocked P7 oligos.
FIG. 1B is a schematic showing an exemplary method described herein using double stranded templates. In (3), each strand of the double-stranded fragment is extended in the presence of a modified nucleotide (uracil is shown as an example). In (4), the extended oligonucleotides are cleaved leaving a reversible block onto the 3' end. In (5), P5-SBS3 oligos are blocked.
FIG. 1C is a schematic showing an exemplary method described herein using double stranded templates. In (6), the block on the extended oligonucleotides is cleaved. In (7), a P7'-SBS8' adapter is ligated to the ends of the extended oligonucleotides. In (8), the block on the P5 and P7 oligos is removed.
FIG. 1D is a schematic showing an exemplary method described herein using double stranded templates. In (9), amplification is performed to generate clusters of nucleic acid sequences.
Figure 1A:
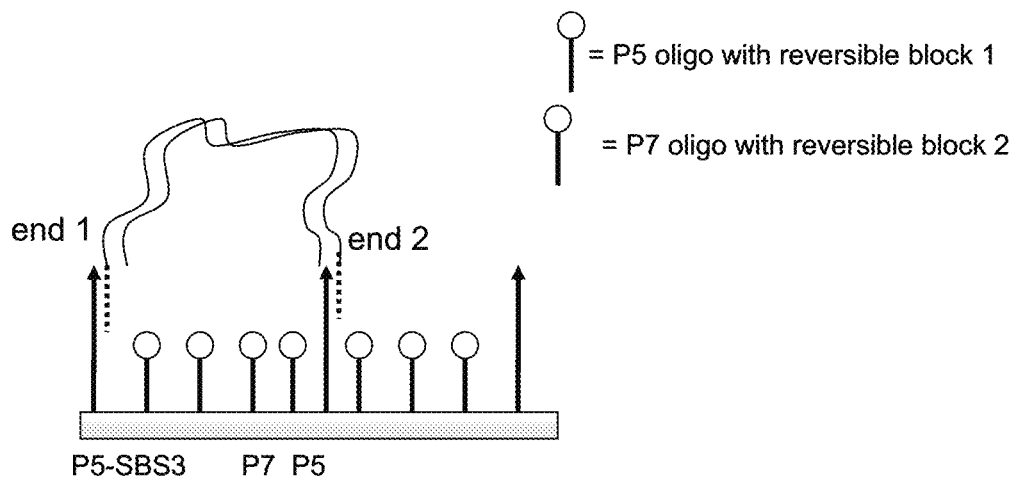
Figure 1B:
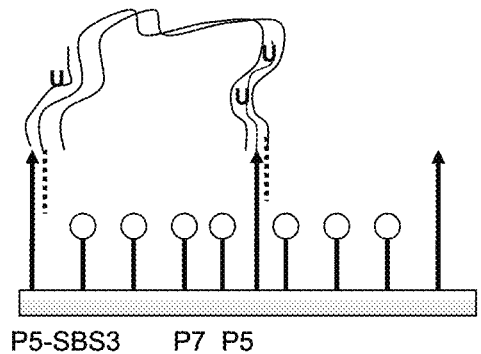
Figure 1B:
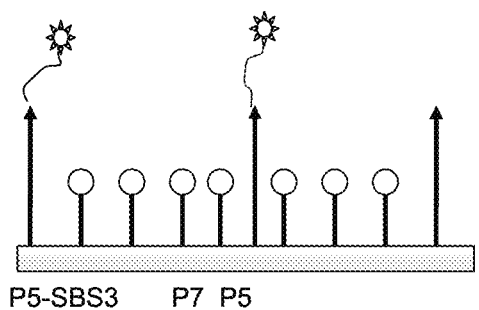
Figure 1B:
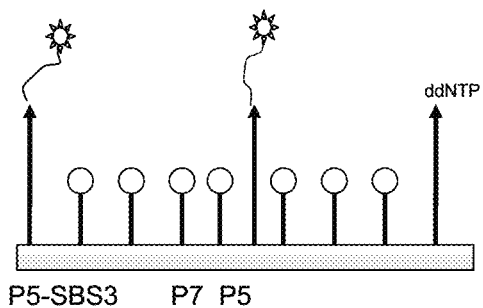
Figure 1C:
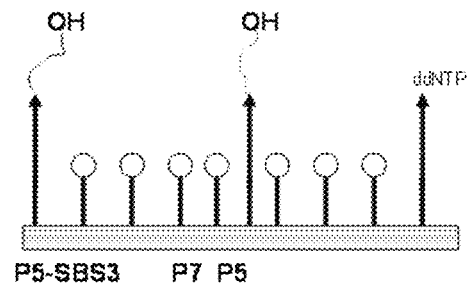
Figure 1C:
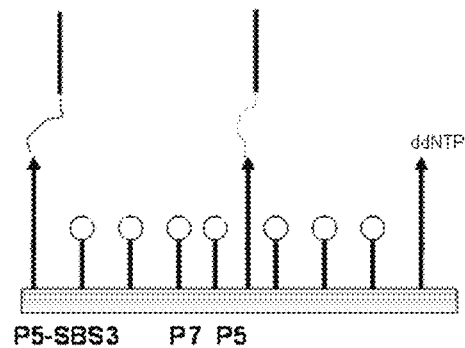
Figure 1C:
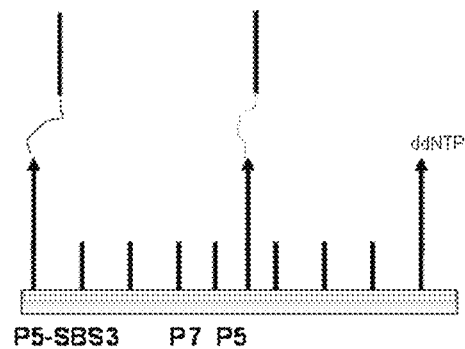
Figure 1D:
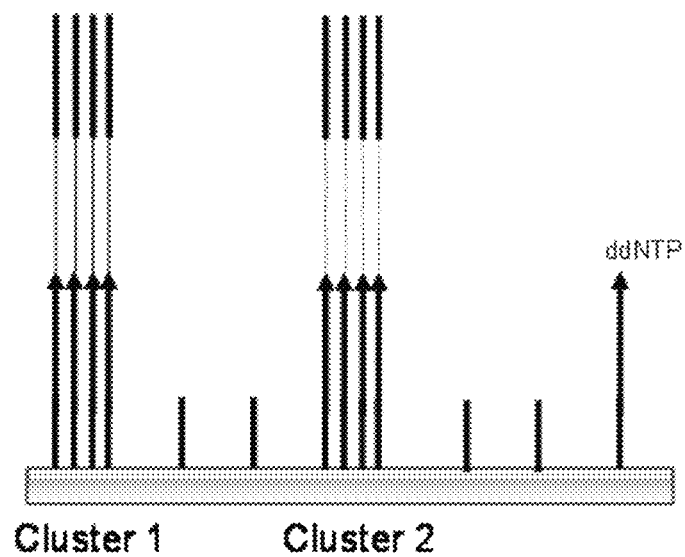
Figure 2:
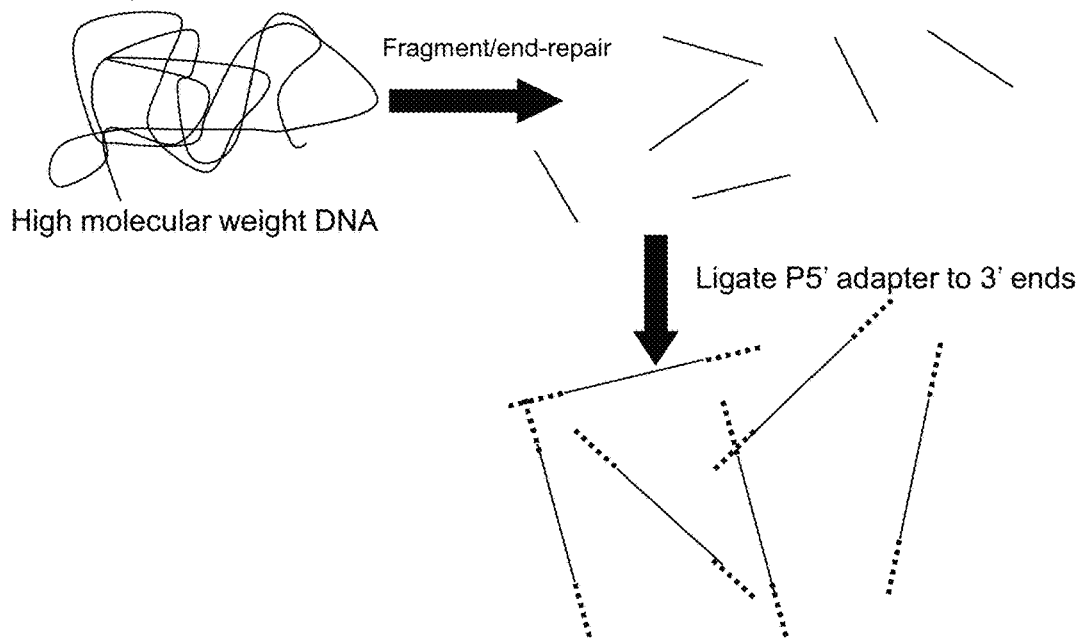
FIG. 2 is a schematic showing an exemplary method of direct sequencing of single double-stranded molecules. In (1), genomic DNA is fragmented into double-stranded fragments followed by ligation of P5' adapters onto the 3' ends of the fragments. In (2), each 3' end of the ligated fragments is attached to a solid surface by hybridizing to P5 oligos. In (3), the P5 oligos on the surface are used as sequencing primers to sequence the two ends of the DNA fragments.
Figure 2:
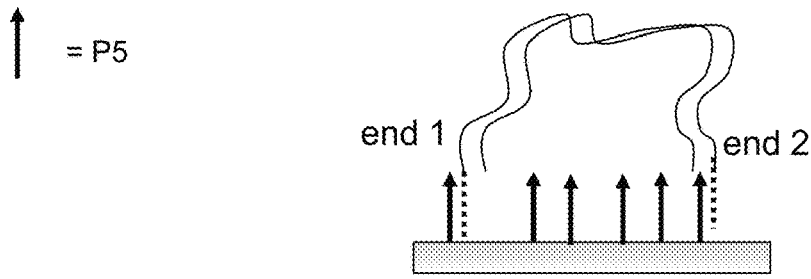
Figure 2:
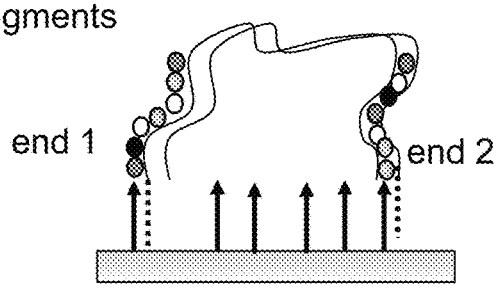
Figure 3A:
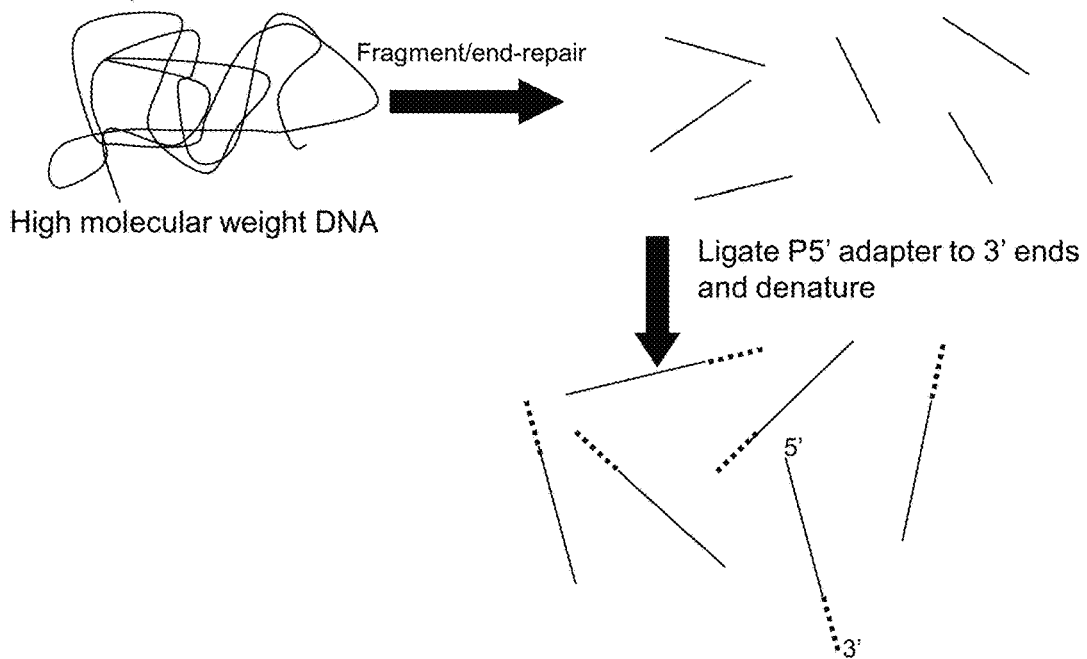
FIG. 3A is a schematic showing an exemplary method of single molecule sequencing after ligation and extension of single stranded molecules using a single primer immobilized to a solid surface. In (1), genomic DNA is fragmented into double-stranded fragments followed by ligation of P5' adapters onto the 3' ends of the fragments. The double-stranded fragments with adapters are then denatured to produce single stranded fragments. In (2), the 5' end of the single-stranded fragment is ligated onto the end of a P5 oligo comprising a modified nucleotide. In (3), the 3' end of the single-stranded fragment is hybridized to a P5 oligo.
Figure 3A:
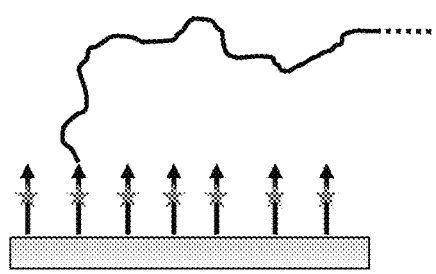
Figure 3A:
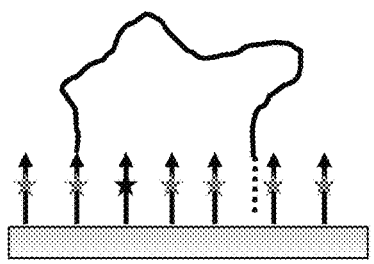
Figure 3B:
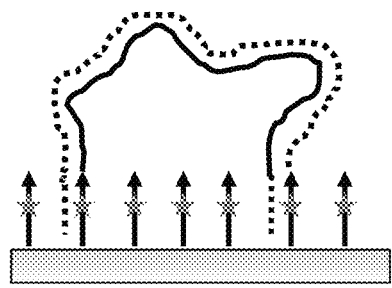
FIG. 3B is a schematic showing an exemplary method of single molecule sequencing after ligation and extension of single stranded molecules using a single primer immobilized to a solid surface. In (4), the P5 oligo hybridized to the 3' end of the single-stranded fragment is extended to form a double-stranded fragment. In (5), the P5 oligo is then cleaved at the modified nucleotide. In (6), the ends of the double-stranded fragment are sequenced using the P5 oligos as sequencing primers.
Figure 3B:
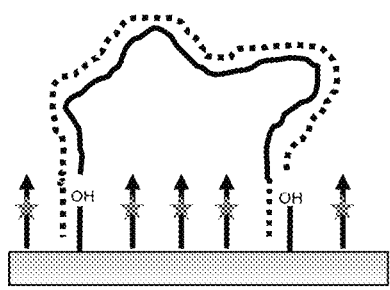
Figure 3B:
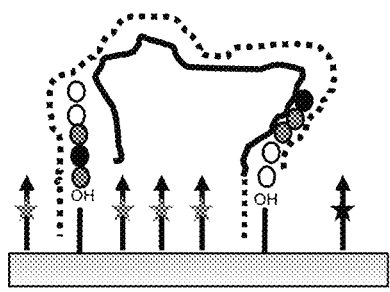
Figure 4A:
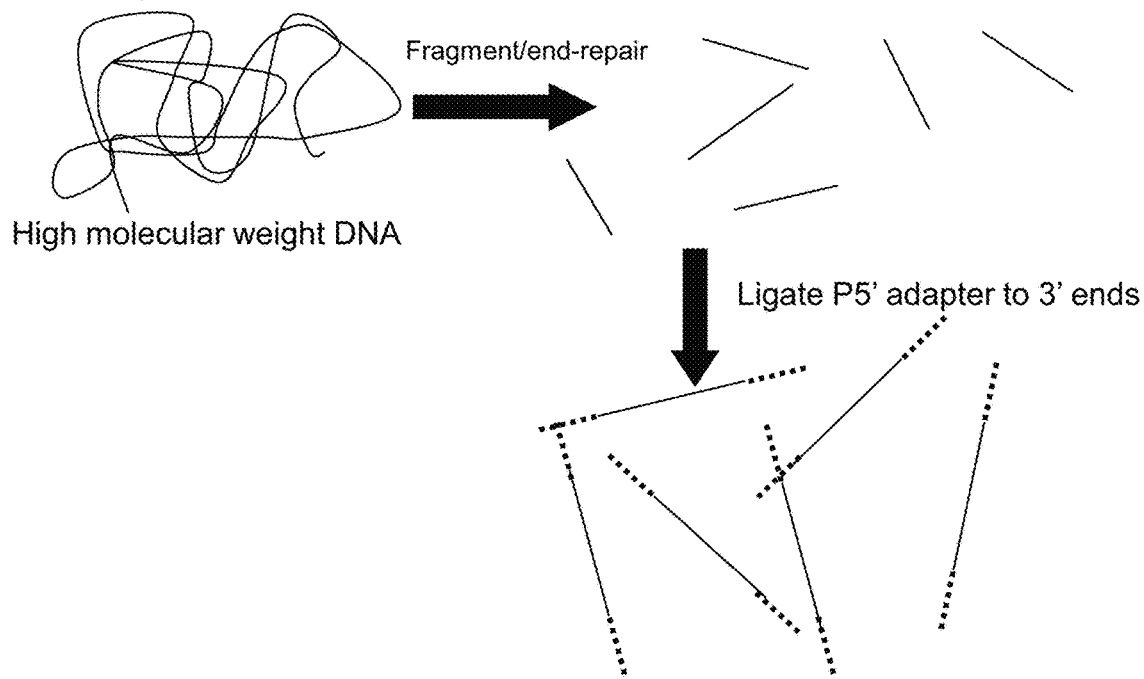
FIG. 4A is a schematic showing an exemplary sequencing method described herein using transposons. In (1), genomic DNA is fragmented into double-stranded fragments followed by ligation of P5' adapters onto 3' ends of the fragments. In (2), the 3' ends of the fragments are hybridized to P5 oligos on a solid surface. In (3), the P5 oligos are partially extended using the double-stranded fragment as a template to generate two extended fragments.
Figure 4A:
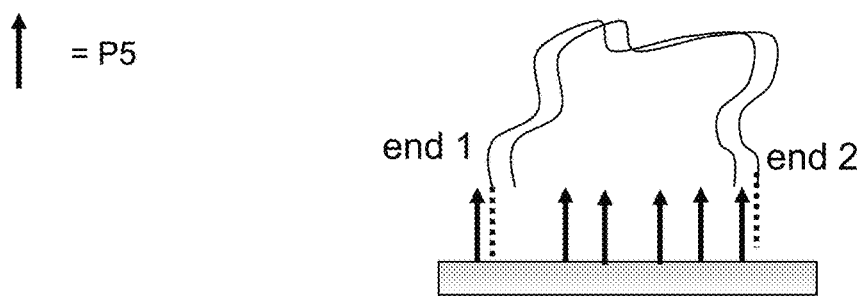
Figure 4A:
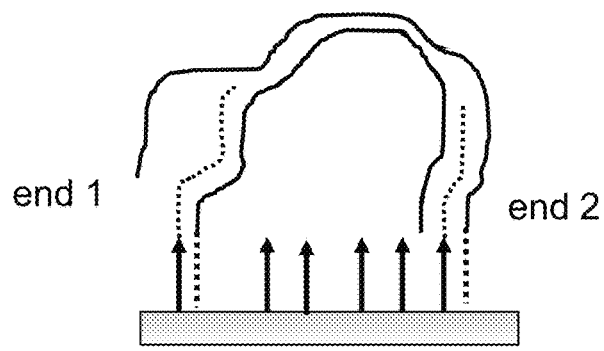
Figure 4B:
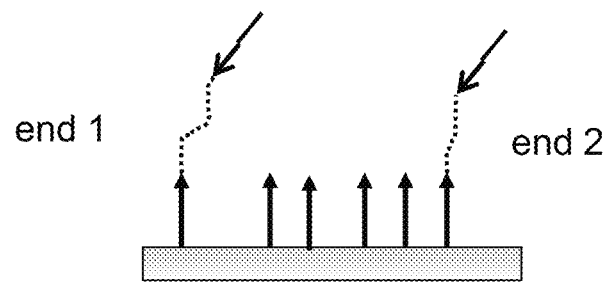
FIG. 4B is a schematic showing an exemplary sequencing method described herein using transposons. In (4), transposon insertion produces two extended fragments with additional nucleic acid sequences (e.g., primers, adapters and/or indexing tags). The fragments can then be sequenced or amplified to produce clusters for sequencing.
Figure 5:
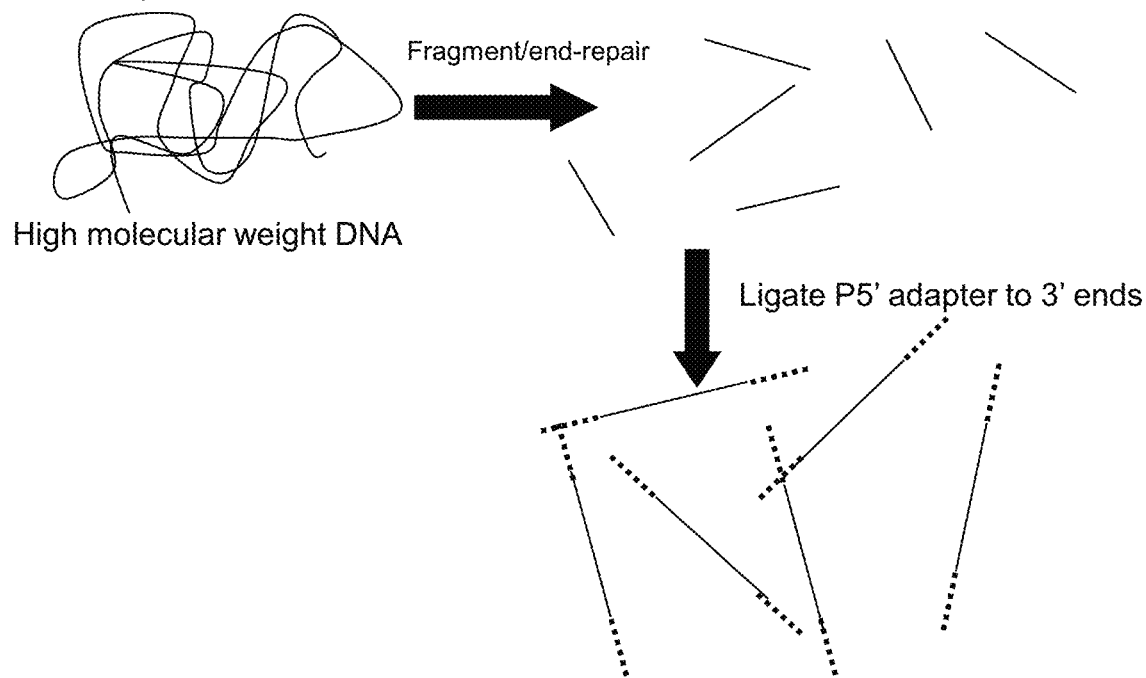
FIG. 5 is a schematic showing another exemplary sequencing method described herein using transposons. In (1), genomic DNA is fragmented into double-stranded fragments followed by ligation of P5' adapters onto 3' ends of the fragments. In (2), the 3' ends are hybridized to P5 oligos on the solid surface followed by ligation of the 5' ends of the fragments to the P5 oligos. In (3), transposon insertion produces two single-stranded fragments representing the ends of the double-stranded fragment. The single-stranded fragments can then be sequenced or amplified to produce clusters for sequencing.
Figure 5:
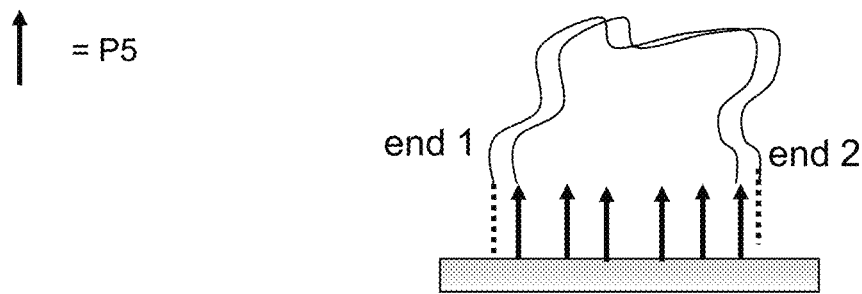
Figure 5:
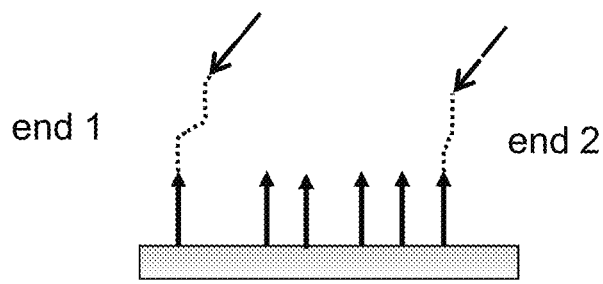
Figure 6B:
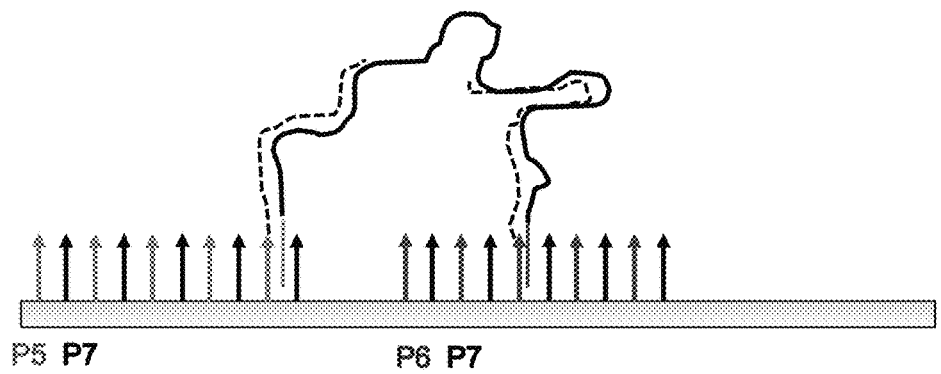
FIG. 6B is a schematic showing another exemplary sequencing method provided herein using a patterned surface. In (4), the P5 and P6 oligos are partially extended using the double-stranded fragment as a template to generate two extended fragments. In (5), transposon insertion produces two extended fragments with additional nucleic acid sequences (e.g., primers, adapters and/or indexing tags), in this case a P7' primer sequence. The fragments can then be sequenced or amplified to produce clusters for sequencing.
Figure 6B:
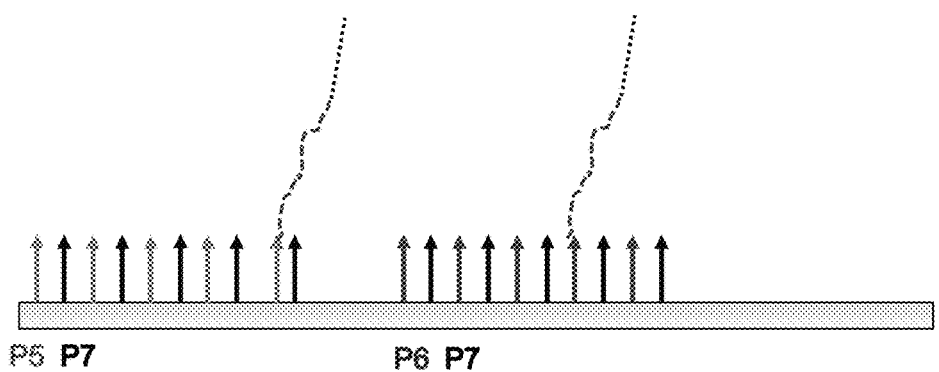

General methods of paired-end sequencing have been described, for example, in Bentley et al., Nature, 456:53-58 (2008); WO 07/010252; WO 07/091077; WO 08/041002 and WO 09/032167, which are incorporated by reference herein in their entireties. Provided herein are methods for obtaining paired end (PE) information from a single read. This is achieved by using DNA fragments of sufficient length such that the two ends of a fragment generate a pair of clusters that tend to be in close proximity. For example, in the provided methods, the DNA molecules are sufficiently long such that the two ends of the DNA molecule are captured on a surface in such a way that they are sufficiently separated from one another so that they can be differentiated, e.g., by the formation of two optically distinct clusters.

The methods described herein advantageously permit simultaneous determination of sequence information for an entire DNA fragment or both ends of a DNA fragment. This will accelerate the rate at which polynucleotide sequence information can be obtained and improve the reliability of such sequence information, including the ability to assign empirically determined nucleotide sequences with greater confidence to specific locations within a larger organizational framework, such as a gene, chromosomal region, chromosome or genome.

Provided herein is a method for sequencing a plurality of polynucleotide molecules. The method includes attaching a plurality of polynucleotide molecules to a surface, wherein each polynucleotide molecule comprises a first and second portion and wherein each polynucleotide molecule is attached under conditions wherein the first portion is attached to a first location of the surface and the second portion is attached to a second location of the surface, separating the first and second portions, sequencing the first and second portions, and comparing the sequences and locations or relative proximities of the first and second portions to determine the sequence of the plurality of polynucleotide molecules.

Thus, provided herein is a method for sequencing a plurality of polynucleotide molecules including the steps of providing a plurality of polynucleotide molecules attached to a surface, wherein a first portion of each polynucleotide molecule is attached to a first location of the surface and a second portion of each polynucleotide molecule is attached to a second location of the surface, the relative proximity of the first and second locations being correlated with the probability that the first and second portions are paired. The method also includes the steps of separating the first and second portions of the polynucleotide molecules on the surface, determining the sequences of the first and second portions of the polynucleotide molecules, and comparing the relative proximities and the sequences to determine which first and second portions are paired and to determine the sequence of the target polynucleotide molecules.

Also provided is a method of sequencing including the steps of providing a plurality of polynucleotide molecules, each polynucleotide molecule comprising a first and second portion of the target polynucleotide molecule, whereby the first and second portions are paired, attaching the plurality of polynucleotide molecules to a surface, wherein the first portion of each polynucleotide molecule is attached to a first location of the surface and the second portion of each polynucleotide molecule is attached to a second location of the surface, the relative proximity of the first and second locations being correlated with the probability that the first and second portions are paired, separating the first and second portions of the polynucleotide molecules on the surface, determining the sequences of the first and second portions of the polynucleotide molecules, comparing the relative proximities of the first portions and the second portions to determine which first and second portions are paired, and using sequences of the paired first and second portions to determine the sequence of the plurality of target polynucleotide molecules.

In another embodiment, provided is a method of sequencing a target polynucleotide molecule including the steps of providing a plurality of polynucleotide molecules, each polynucleotide molecule comprising a first portion and a second portion of the target polynucleotide molecule, wherein the first and second portions are paired, attaching the plurality of polynucleotide molecules to a surface, wherein the first portion of each polynucleotide molecule is attached to a first location of the surface and the second portion of each polynucleotide molecule is attached to a second location of the surface, the proximity of the first and second locations being correlated with the probability that the first and second portions are paired, separating the first and second portions of the polynucleotide molecules thereby unpairing the first and second portions, sequencing the first and second portions of the polynucleotide molecules, comparing, at a first location, the sequence of a first or second portion to the sequences of first and second portions at locations in proximity to the first location, and repeating the comparing step to determine which first and second portions are paired and to determine the sequence of the target polynucleotide molecule.

As used throughout, the terms "paired" and "linked" when in reference to portions of polynucleotide molecules means that the portions occur on a single polynucleotide molecule (e.g., the same gene, chromosome, etc.) and are, thus, linked or paired in the genome. By way of example, after fragmentation of a plurality of polynucleotide molecules, the fragments will contain paired portions, i.e., portions that come from the same polynucleotide molecule. The paired portions at the two ends of the fragments are known to be located on the same polynucleotide molecule (e.g., gene, chromosome, and the like) approximately the length of the fragment apart. This information facilitates, for example, the assembly of a single polynucleotide sequence, a plurality of polynucleotide sequences, and the like.

In the methods described throughout, the first and second portions are preferably separated after being attached to the surface. Optionally, the first and second portions are noncontiguous portions. As used throughout, the term "noncontiguous" means that the polynucleotide molecule comprises two or more sequences that belong to the same template or target polynucleotide molecule, wherein the sequences are not adjacent on the polynucleotide molecule. For example, a polynucleotide molecule contains two noncontiguous portions that come from the same chromosome, but the noncontiguous portions are not located adjacent to one another on the polynucleotide molecule or on the chromosome. Alternatively, the first and second portions are located adjacent to one another on the sample polynucleotide molecule or chromosome.

In the methods described herein, the step of comparing the sequences and locations can include using the knowledge that the portions are likely to be located in locations closer together than locations containing unlinked sequences (i.e., sequences not on the same template or polynucleotide molecule that was attached to the surface, e.g., the same fragment). Optionally, the step of comparing the sequences and locations includes using an algorithm that takes into account the first and second portions in relative proximities are more likely to be paired or comprise sequences from the same polynucleotide molecule (e.g., from the same chromosome) or fragment thereof. For example, the distance between the first and second portions on the surface is positively correlated with the probability that the first and second portions are from the same polynucleotide molecule.

Optionally, the step of comparing the sequences and locations includes the use of indexing tags to identify locations containing linked or paired sequences (i.e., sequences on the same template or polynucleotide molecule, e.g., the same fragment). Thus, the step of comparing the sequences and locations of the portions may include the use of indexing tags to identify portions containing linked sequences (i.e., sequences on the same template or polynucleotide molecule, e.g., the same fragment). For example, a polynucleotide molecule comprising first and second portions may contain the same or a different indexing tag on both the first and second portions. This can be accomplished, for example, by ligating indexing tags to the ends of a polynucleotide molecule comprising the first and second portions. Optionally, the first and second portions retain the tag after separation of the portions.

The step of comparing the sequences and relative proximities (or locations) of the portions may include use of the knowledge that the size of a cluster (generation from a single portion) is positively correlated with the size of the nucleic acid molecule used to generate the cluster. For example, a nucleic acid molecule of 100 nucleotides in length will generate a cluster of a size larger than a nucleic acid molecule of 50 nucleotides in length. Thus, if the first and second portions of a polynucleotide molecule differ in length, upon separation, the first and second portions will generate clusters of different sizes proportional to the length of the first and second portions. By way of example, if a polynucleotide molecule is 4000 base pairs in length and it is divided into a first portion of 500 nucleotides in length and a second portion of 3500 nucleotides in length, the cluster comprising the first portion will be smaller than the cluster comprising the second portion. This information can be exploited to identify clusters likely to contain linked sequences (i.e., the first and second portions from the same target polynucleotide molecule). As described in more detail below, the first and second clusters on the surface may be spatially correlated based on the length of the polynucleotide molecule.

By way of further example, a method for sequencing a target polynucleotide molecule can include the steps of attaching a plurality of polynucleotide molecules to a surface, wherein each polynucleotide molecule comprises a first and second portion from the target polynucleotide molecule and wherein each polynucleotide molecule is attached under conditions wherein the first portion is attached to a first area of the surface and the second portion is attached to a second area of the surface, separating the first and second portions of the polynucleotide molecules, sequencing the first and second portions of the polynucleotide molecules, comparing the sequences of the first portions and the locations of the first areas to the locations of the second areas and the sequences of the second portions to determine the sequence of the target polynucleotide molecule. Optionally, the first and second portions are noncontiguous portions. Optionally, the target polynucleotide molecule is fragmented and the fragments are used to generate the plurality of polynucleotide molecules, wherein each polynucleotide molecule comprises a first and second portion from the same fragment. Optionally, the portions are separated by extending the attached polynucleotide molecules under conditions to incorporate cleavable sites into the extended polynucleotide molecules and cleaving the sites of the extended oligonucleotide molecules to separate the first and second portions. The extension can be carried out in the presence of one or more modified nucleotides, for example, uracil or 8-oxo-guanine. Optionally, the surface comprises a plurality of first oligos comprising a reversible block and a plurality of second, unblocked oligos to which the polynucleotide molecules attach. Optionally, after the first and second portions are separated an adapter is ligated onto the first and second portions followed by unblocking of the first oligos. Optionally, the adapters bind to the first oligos and the first and second portions are amplified to produce multiple copies of the first and second portions in the first and second areas.

By way of another example, a method for sequencing a genome includes the steps of providing a surface comprising a plurality of clusters comprising polynucleotide molecules, wherein each cluster comprises polynucleotide molecules of the same sequence, determining the sequence of the polynucleotide molecules in the clusters, comparing the sequence of polynucleotide molecules in a first cluster to the sequence of polynucleotide molecules in a second cluster and comparing the locations of the first and second clusters on the surface, and repeating the comparing step to determine the sequence of the genome. Optionally, each cluster is located at a known location on the surface. Optionally, the polynucleotide molecules in the clusters are generated from one or more target polynucleotide molecules. The clusters can be generated by (i) attaching a plurality of polynucleotide molecules to the surface, wherein each polynucleotide molecule comprises a first and second portion and wherein each polynucleotide molecule is attached under conditions wherein the first portion is attached to a first area of the surface and the second portion is attached to a second area of the surface, (ii) separating the first and second portions, and (iii) amplifying the first and second portions to produce the plurality of clusters. The plurality of polynucleotide molecules can be produced by fragmenting one or more target polynucleotide molecules and using the fragments to generate the plurality of polynucleotide molecules, wherein each polynucleotide molecule comprises a first and second portion from the same fragment. Optionally, the first and second portions are noncontiguous. As described throughout, the distance between the first and second clusters on the surface is positively correlated with the probability that the first and second clusters are from the same target polynucleotide molecule. For example, the shorter the distance between the first and second clusters indicates that the first and second clusters comprise polynucleotide molecules of sequences from the same target polynucleotide molecule.

As used throughout, oligonucleotides or polynucleotide molecules include deoxyribonucleic acids (DNA), ribonucleic acids (RNA) or other form of nucleic acid. The polynucleotide molecule can be any form of natural, synthetic or modified DNA, including, but not limited to, genomic DNA, copy DNA, complementary DNA, or recombinant DNA. Alternatively, the polynucleotide molecule can be any form of natural, synthetic or modified RNA, including, but not limited to mRNA, ribosomal RNA, microRNA, siRNA or small nucleolar RNA. The polynucleotide molecule can be partially or completely in double-stranded or single-stranded form. The terms "nucleic acid," "nucleic acid molecule," "oligonucleotide," and "polynucleotide" are used interchangeably throughout. The different terms are not intended to denote any particular difference in size, sequence, or other property unless specifically indicated otherwise. For clarity of description the terms may be used to distinguish one species of molecule from another when describing a particular method or composition that includes several molecular species.

As used throughout, the term "target polynucleotide molecule" refers to the molecule used to generate the plurality of polynucleotide molecules that is attached to a surface. Target polynucleotide molecules can be any molecule to be sequenced. For example, the polynucleotide molecule can be a plasmid, a gene, chromosomal region, chromosome or genome. In the context of genome or whole genome sequencing, a plurality of target polynucleotide molecules (e.g., a plurality of chromosomes) can be used to generate the plurality of polynucleotide molecules.

Polynucleotide molecules or nucleic acids for use in the provided methods may be obtained from any biological sample using known, routine methods. Suitable biological samples include, but are not limited to, a blood sample, biopsy specimen, tissue explant, organ culture, biological fluid or any other tissue or cell preparation, or fraction or derivative thereof or isolated therefrom. The biological sample can be a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like. For example, polynucleotide molecules may be obtained from primary cells, cell lines, freshly isolated cells or tissues, frozen cells or tissues, paraffin embedded cells or tissues, fixed cells or tissues, and/or laser dissected cells or tissues. Biological samples can be obtained from any subject or biological source including, for example, human or non-human animals, including mammals and non-mammals, vertebrates and invertebrates, and may also be any multicellular organism or single-celled organism such as a eukaryotic (including plants and algae) or prokaryotic organism, archaeon, microorganisms (e.g. bacteria, archaea, fungi, protists, viruses), and aquatic plankton.

The polynucleotide molecule, target polynucleotide molecule or fragments described herein can be of any length suitable for use in the provided methods. For example, the polynucleotide molecules or fragments can be at least 10, at least 20, at least 30, at least 40, at least 50, at least 50, at least 100, at least 150, at least 200, at least 250, at least 500, or at least 1000 nucleotides in length. Optionally, the polynucleotide molecule or fragment is 150 to 4000 nucleotides in length, 500 to 3000 nucleotides in length, or 1000 to 2000 nucleotides in length. By way of another example, the target polynucleotide molecules can be, for example, at least 1 kilobase in length, at least 10 kilobases in length, at least 20 kilobases in length, at least 30 kilobases in length, at least 40 kilobases in length, at least 50 kilobases in length, at least 60 kilobases in length, at least 70 kilobases in length, at least 80 kilobases in length, at least 90 kilobases in length, at least 100 kilobases in length, or longer.

A plurality of polynucleotide molecules can be prepared by fragmenting one or more polynucleotide molecules and using the fragments to generate the plurality of polynucleotide molecules comprising the first and second portions. Preferably, the first and second portions are from the same fragment. In the provided methods described herein, the first and second portions are, optionally, located at the opposite ends of the polynucleotide molecules (e.g., the 5' and 3' ends). The number of nucleotides between the first and second portions may be substantially the same for each polynucleotide molecule. Optionally, the first and second portions are noncontiguous portions.

The plurality of polynucleotide molecules may be prepared using a variety of standard techniques available and known. Exemplary methods of polynucleotide molecule preparation include, but are not limited to, those described in Bentley et al., Nature 456:49-51 (2008); U.S. Pat. No. 7,115,400; and U.S. Patent Application Publication Nos. 2007/0128624; 2009/0226975; 2005/0100900; 2005/0059048; 2007/0110638; and 2007/0128624, each of which is herein incorporated by reference in its entirety. For example, polynucleotide molecules are modified to comprise one or more regions of known sequence (e.g., an adapter and/or an indexing tag) located on the 5' and/or 3' ends. Optionally, the adapter comprises the indexing tag. When the polynucleotide molecules comprise known sequences on the 5' and 3' ends, the known sequences can be the same or different sequences. Optionally, as described more fully below, a known sequence located on the 5' and/or 3' ends of the polynucleotide molecules is capable of hybridizing to one or more oligonucleotides immobilized on a surface. For example, a polynucleotide molecule comprising a 5' known sequence may hybridize to a first plurality of oligonucleotides while the 3' known sequence may hybridize to a second plurality of oligonucleotides. Optionally, polynucleotide molecules comprise one or more detectable labels. The one or more detectable labels may be attached to the nucleic acid template at the 5' end, at the 3' end, and/or at any nucleotide position within the nucleic acid template. The polynucleotide molecules for use in the provided methods comprise the nucleic acid to be amplified and/or sequenced and, optionally, short nucleic acid sequences at the 5' and/or 3' end(s).

A short nucleic acid sequence that is added to the 5' and/or 3' end of a nucleic acid can be a universal sequence. A universal sequence is a region of nucleotide sequence that is common to, i.e., shared by, two or more nucleic acid molecules, where the two or more nucleic acid molecules also have regions of sequence differences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize specifically to such a universal sequence. The target nucleic acid sequence-bearing molecules may be modified to attach universal adapters (e.g., non-target nucleic acid sequences) to one or both ends of the different target sequences, the adapters providing sites for hybridization of universal primers. This approach has the advantage that it is not necessary to design a specific pair of primers for each template to be generated, amplified, sequenced, and/or otherwise analyzed; a single pair of primers can be used for amplification of different templates provided that each template is modified by addition of the same universal primer-binding sequences to its 5' and 3' ends.

The polynucleotide molecules can be modified to include any nucleic acid sequence desirable using standard, known methods. Such additional sequences may include, for example, restriction enzyme sites, or oligonucleotide indexing tag in order to permit identification of amplification products of a given nucleic acid sequence. As described herein, the indexing tag can be added to a polynucleotide molecule by inclusion on an adapter or on a transposon. Optionally, the indexing tag can be directly ligated to the ends of a polynucleotide molecule.

Optionally, the surface comprises one or more pluralities of oligonucleotide molecules. The terms "oligonucleotides," "oligonucleotide molecules" and "oligos" are used throughout interchangeably. By way of example, the surface can comprise a first, second, third, fourth, or more pluralities of oligonucleotide molecules each plurality having a different sequence. It will be understood that different pluralities of oligonucleotides can share a common sequence so long as there is a sequence difference between at least a portion of the different pluralities. For example, as shown in FIG. 1, the two oligos identified as P5 and P5-SBS3 share a common sequence P5, but the P5-SBS3 has an additional sequence not found on the P5 oligo. Thus, a first plurality of oligonucleotides can share a sequence with a second plurality of oligonucleotides as long as the oligos in one plurality have a different sequence not found in the oligos of the other plurality.

Once the plurality of polynucleotide molecules is prepared, one or more of the polynucleotide molecules in the plurality of polynucleotide molecules can be attached to a surface. The one or more of the polynucleotide molecules can be attached to the surface under conditions wherein the first portion is attached to a first location of the surface and the second portion is attached to a second location of the surface.

The polynucleotide molecules can be attached to the surface by hybridization or binding to a plurality of oligos. Optionally, the polynucleotide molecules are attached to the surface by attaching one end of the polynucleotide molecule to the surface or to the end of the oligos (e.g., by ligation). Hybridization is accomplished, for example, by ligating an adapter to the ends of the polynucleotide molecules. The nucleic acid sequence of the adapter can be complementary to the nucleic acid sequence of the oligo, thus, allowing the adapter to bind or hybridize to the oligos on the surface. Optionally, the polynucleotide molecules are single or double stranded and adapters are added to the 5' and/or 3' ends of the polynucleotide molecules. Optionally, the polynucleotide molecules are double-stranded and adapters are ligated onto the 3' ends of double-stranded polynucleotide molecule. Optionally, polynucleotide molecules are used without any adapter.

By way of another example, the surface comprises a plurality of first oligos to which the polynucleotide molecules attach and a plurality of second oligos comprising a reversible block. As described above, the polynucleotide molecules can hybridize to the first oligos through an adapter. After the first and second portions are separated, a second adapter can be ligated onto the ends of the first and second portions. In this aspect, this part of the sample prep can take place inside the flowcell. The nucleic acid sequence of the second adapter can be complementary to the nucleic acid sequence of the second oligo. The second oligos can be unblocked and the second adapters can bind to the second oligos. The first and second portions can then be amplified to produce multiple copies of the first and second portions in the first and second locations. Thus, the first and second locations can be clusters of polynucleotide molecules comprising first and second portions. Optionally, the first oligos, second oligos or adapters comprise an oligonucleotide indexing tag.

By way of a third example, the surface comprises a plurality of first oligos to which the polynucleotide molecules attach and a plurality of second and third oligos comprising a reversible block. After the polynucleotide molecules attach to the surface through hybridization to the first oligos, the polynucleotide molecule can be extended. If double-stranded, each strand of the double-stranded polynucleotide molecule can be extended, e.g., in the presence of a modified nucleotide, in order to facilitate separation of the first and second portions of the polynucleotide molecules. After the first and second portions are separated, a second adapter can be ligated to the ends of the extended first and second portions followed by removal of the blocks from the second and third oligos. The first and second portions can then be amplified to produce multiple copies of the first and second portions in discrete locations referred to herein as clusters. Optionally, the first oligos, second oligos, third oligos or adapters comprise an oligonucleotide indexing tag.

By way of another example, the surface is a patterned surface and comprises a two or more types of patches. A first type of patch contains a plurality of first oligos and a plurality of second oligos. The second type of patch contains a plurality of the second oligos and a plurality of third oligos. Polynucleotide molecules are hybridized such that one end of the molecules hybridizes to a first patch and the other end of the molecule hybridizes to a second patch. After the first and second portions are separated, they can then be sequenced or amplified to produce clusters for sequencing.

A surface or support for use in the provided methods described herein refers to any surface or collection of surfaces to which nucleic acids can be attached. Suitable surfaces include, but are not limited to, beads, resins, gels, wells, columns, chips, flowcells, membranes, matrices, plates or filters. For example, the surface can be latex or dextran beads, polystyrene or polypropylene surfaces, polyacrylamide gels, gold surfaces, glass surfaces, optical fibers, or silicon wafers. Optionally, the surface is three dimensional, for example, a three dimensional matrix. The surface can be any material that is amenable to linkage to a nucleic acid.

Optionally, the surface is contained in a vessel or chamber such as a flow cell, allowing convenient movement of liquids across the surface to enable the transfer of reagents. Exemplary flow cells that can be used in this manner are described in WO 2007/123744, which is incorporated herein by reference in its entirety.

Optionally, the surface may comprise a layer or coating of a material with reactive groups permitting attachment of polynucleotides. The polynucleotides are then attached to the material (e.g., covalently), which is attached to the surface (e.g., noncovalently). Such a surface is described in WO 05/65814, which is incorporated by reference herein in its entirety.

The term "immobilized" as used herein is intended to encompass direct or indirect attachment to a solid support via covalent or non-covalent bond(s). In particular embodiments, all that is required is that the molecules (for example, nucleic acids) remain immobilized or attached to a support under conditions in which it is intended to use the support, for example in applications requiring nucleic acid amplification and/or sequencing. For example, oligonucleotides are immobilized such that a 3' end is available for enzymatic extension and/or at least a portion of the sequence is capable of hybridizing to a complementary sequence. Immobilization can occur via hybridization to a surface attached oligonucleotide, in which case the immobilized oligonucleotide or polynucleotide may be in the 3'-5' orientation. Alternatively, immobilization can occur by means other than base-pairing hybridization, such as the covalent attachment.

In particular embodiments, the attached polynucleotide molecules comprise a cleavable site to separate the first and second portions. For example, the attached polynucleotide molecules can be extended under conditions to incorporate cleavable sites into the extended polynucleotide molecules and cleaving the sites of the extended oligonucleotide molecules to separate the first and second portions. Various cleavage methods may be used in accordance with the provided methods to cleave one or both strands of the polynucleotide molecules. Optionally, the cleavable site comprises a modified nucleotide or a restriction enzyme site. Such methods are known and include those described in U.S. Publication No. 20090118128, which is incorporated by reference herein in its entirety. For example, chemical cleavage may be used, which encompasses any method using a non-enzymatic chemical reagent in order to promote/achieve cleavage of a polynucleotide molecule whether in single or double stranded form. The polynucleotide molecule can include one or more non-nucleotide chemical moieties and/or non-natural nucleotides and/or non-natural backbone linkages in order to permit a chemical cleavage reaction at a pre-determined cleavage site. By way of example, in the provided methods, the extension is carried out in the presence of one or more types of modified nucleotides. Nucleotides for use in the provided methods include, for example, derivatives capable of being selectively cleaved in a nucleic acid strand. Such nucleotides include, but are not limited to, uracil or 8-oxo guanine. Optionally, two types of modified nucleotides can be used (e.g., uracil and 8-oxo guanine, e.g., to reduce GC bias). These modified nucleotides can be modified to abasic sites by the actions of Uracil DNA glycosylase (UDG) and formamidopyrimidine ##fapy ##-DNA glycosylase (FPG), respectively. The polynucleotide strand including the abasic site may then be cleaved at the abasic site by treatment with endonuclease (e.g. EndoIV endonuclease, AP lyase, FPG glycosylase/AP lyase, and EndoVIII glycosylase/AP lyase), heat or alkali. FPG alone can also result in abasic site cleavage.

The provided methods may make use of non-extendable nucleotides which act as terminators and prevent further strand elongation. Such terminators may be permanent (e.g., dideoxyribose analogues such as ddTTP or ddATP) or reversible. Reversible terminators may contain any moiety which acts to block polymerase extension, but can subsequently be altered to allow polymerase extension. Suitable reversible terminator moieties include blocking groups on the nucleotide 3' hydroxyl. There is a variety of known 3' hydroxyl blocking moieties that are capable of acting as reversible polymerase blocks, including the allyl, methoxymethyl, azidomethyl or O—NH2 groups. Optionally, terminator moieties are attached to nucleotide bases at 2' or 4' positions. Examples of nucleotide terminators can be found in U.S. Pat. Nos. 5,302,509; 7,057,026; 6,664,079; 7,541,444; and 7,544,794, the contents of which are incorporated by reference herein in their entireties. If desired, reversible terminators may be removed to allow subsequent polymerase action on the strands, for example to synthesize full length strands at the end of the amplification process.

The modified nucleotides are typically provided at a concentration effective to generate immobilized polynucleotide molecules of an appropriate size. Such concentrations may be determined empirically by those of skill in the art. For example, the concentration of modified nucleotides may be determined based on the ability of a polymerase to incorporate the modified nucleotide and/or based on the desired length of the fragment to be left after cleavage. For example, the modified nucleotides are provided at a concentration ratio of 1 to 100. By way of example, if uracil is used, for every 100 units of dTTP supplied, 1 unit of dUTP is supplied.

Alternatively, the first and second portions can be separated through use of a transposon. As used herein, the term transposon refers to the nucleic acid sequence containing the transposon elements together with all of the nucleic acid sequence between the elements. Transposons may comprise a cleavable element such as a modified nucleotide or a restriction enzyme site. Optionally, the transposon may also comprise an indexing tag. Transposons generally require only the transposase protein and a cognate transposon. The transposase may be purified from natural sources or it may be produced in vitro or synthesized by methods known in the art. Transposase may be expressed in bacterial, yeast, insect or mammalian cells or produced in cell-free expression systems. The transposase may have a wild-type amino acid sequence or it may have a modified amino acid sequence. Modifications include mutations that affect the activity or stability of the transposase or add functionality to the transposase. Suitable transposon systems useful in the provided methods include, but are not limited to, Sleeping Beauty, To12, PiggyBac, Frog Prince, Minos, and Hsmarl. Transposons also include transposable elements found in prokaryotes such as insertion sequences (IS), transposons (Tn), or bacteriophages such as Mu and D108. Eukaryotic transposable elements include, but are not limited to: Copia elements, TY elements, Tal and Tnt 1 transposable elements, TAP, Tam or Cin transposable elements, and AC, Spm, Bs, CM, Dt, and Mutator transposable elements. In particular embodiments, a synthetic transposable element is used that lacks a functional transposase but which is supplied in trans.

In particular embodiments, the polynucleotide molecules are double stranded and the two strands of the polynucleotide molecules are separated by denaturing the strands of the polynucleotide molecules. Each of the denatured or separated strands of the polynucleotide molecules can then be amplified, e.g., to produce a plurality of clusters. Clusters are described in more detail below.

In other embodiments, the first and second portions are separated by extending the primers hybridized to the double stranded polynucleotide molecules for a period of time sufficient to produce copies of the first and second portions. The first and second portion copies remain immobilized while the double stranded polynucleotide molecules are removed (e.g., by washing). The first and second portions are then amplified, e.g., to generate clusters for sequencing or are directly sequenced.

In the provided methods, after the first and second portions are separated, the first and second portions can be amplified prior to sequencing to produce multiple copies of the first and second portions at the first and second locations. Nucleic acid amplification includes the process of amplifying or increasing the numbers of a nucleic acid template and/or of a complement thereof that are present, by producing one or more copies of the template and/or its complement. In the provided methods, amplification can be carried out by a variety of known methods under conditions including, but not limited to, thermocycling amplification or isothermal amplification. For example, methods for carrying out amplification are described in U.S. Publication No. 2009/0226975; WO 98/44151; WO 00/18957; WO 02/46456; WO 06/064199; and WO 07/010251; which are incorporated by reference herein in their entireties. Briefly, in the provided methods, amplification can occur on the surface to which the polynucleotide molecules are attached. This type of amplification can be referred to as solid phase amplification, which when used in reference to nucleic acids, refers to any nucleic acid amplification reaction carried out on or in association with a surface (e.g., a solid support). For example, all or a portion of the amplified products are synthesized by extension of an immobilized primer. Solid phase amplification reactions are analogous to standard solution phase amplifications except that at least one of the amplification oligonucleotides is immobilized on a surface (e.g., a solid support).

Solid-phase amplification may comprise a nucleic acid amplification reaction comprising only one species of oligonucleotide primer immobilized to a surface. Alternatively, the surface may comprise a plurality of first and second different immobilized oligonucleotide primer species. Solid-phase amplification may comprise a nucleic acid amplification reaction comprising one species of oligonucleotide primer immobilized on a solid surface and a second different oligonucleotide primer species in solution. Solid phase nucleic acid amplification reactions generally comprise at least one of two different types of nucleic acid amplification, interfacial and surface (or bridge) amplification. For instance, in interfacial amplification the solid support comprises a template polynucleotide molecule that is indirectly immobilized to the solid support by hybridization to an immobilized oligonucleotide primer, the immobilized primer may be extended in the course of a polymerase-catalyzed, template-directed elongation reaction (e.g., primer extension) to generate an immobilized polynucleotide molecule that remains attached to the solid support. After the extension phase, the nucleic acids (e.g., template and its complementary product) are denatured such that the template polynucleotide molecule is released into solution and made available for hybridization to another immobilized oligonucleotide primer. The template polynucleotide molecule may be made available in 1, 2, 3, 4, 5 or more rounds of primer extension or may be washed out of the reaction after 1, 2, 3, 4, 5 or more rounds of primer extension.

In surface (or bridge) amplification, an immobilized polynucleotide molecule hybridizes to an immobilized oligonucleotide primer. The 3' end of the immobilized polynucleotide molecule provides the template for a polymerase-catalyzed, template-directed elongation reaction (e.g., primer extension) extending from the immobilized oligonucleotide primer. The resulting double-stranded product "bridges" the two primers and both strands are covalently attached to the support. In the next cycle, following denaturation that yields a pair of single strands (the immobilized template and the extended-primer product) immobilized to the solid support, both immobilized strands can serve as templates for new primer extension.

Optionally, amplification of the first and second portions results in clustered arrays of nucleic acid colonies, analogous to those described in U.S. Pat. No. 7,115,400; U.S. Publication No. 2005/0100900; WO 00/18957; and WO 98/44151, which are incorporated by reference herein in their entireties. Thus, the first and second portions can be amplified to produce a plurality of clusters. Clusters and colonies are used interchangeably and refer to a plurality of copies of a nucleic acid sequence and/or complements thereof attached to a surface. Typically, the cluster comprises a plurality of copies of a nucleic acid sequence and/or complements thereof, attached via their 5' termini to the surface. For example, as described herein, a plurality of pairs of clusters comprising noncontiguous sequences are attached to a surface. The copies of nucleic acid sequences making up the clusters may be in a single or double stranded form.

The clusters can have different shapes, sizes and densities depending on the conditions used. For example, clusters can have a shape that is substantially round, multi-sided, donut-shaped or ring-shaped. The diameter or maximum cross section of a cluster can be from about 0.2 μm to about 6 μm, about 0.3 μm to about 4 μm, about 0.4 μm to about 3 μm, about 0.5 μm to about 2 μm, about 0.75 μm to about 1.5 μm, or any intervening diameter. Optionally, the diameter or maximum cross section of a cluster can be at least about 0.5 μm, at least about 1 μm, at least about 1.5 μm, at least about 2 μm, at least about 2.5 μm, at least about 3 μm, at least about 4 μm, at least about 5 μm, or at least about 6 μm. The diameter of a cluster may be influenced by a number of parameters including, but not limited to, the number of amplification cycles performed in producing the cluster, the length of the nucleic acid template, the GC content of the nucleic acid template or the density of primers attached to the surface upon which clusters are formed. The density of clusters can be in the range of at least about $0.1/mm^2$, at least about $1/mm^2$, at least about $10/mm^2$, at least about $100/mm^2$, at least about $1,000/mm^2$, at least about $10,000/mm^2$ to at least about $100,000/mm^2$. Optionally, the clusters have a density of, for example, $100,000/mm^2$ to $1,000,000/mm^2$ or $1,000,000/mm^2$ to $10,000,000/mm^2$. Clusters may be detected, for example, using a suitable imaging means, such as, a confocal imaging device or a charge coupled device (CCD) camera. Exemplary imaging devices include, but are not limited to, those described in U.S. Pat. Nos. 7,329,860; 5,754,291; and 5,981,956; and WO 2007/123744, each of which is herein incorporated by reference in its entirety. The imaging means may be used to determine a reference position in a cluster or in a plurality of clusters on the surface, such as the location, boundary, diameter, area, shape, overlap and/or center of one or a plurality of clusters (and/or of a detectable signal originating therefrom). Such a reference position may be recorded, documented, annotated, converted into an interpretable signal, or the like, to yield meaningful information. For example, the reference position can be interpreted by the imaging device as a signal that may be generated from two or more adjacent, neighboring or proximal clusters, for example, in order to assist in distinguishing (i) adjacent clusters that are the products of extension from and amplification of first and second non-contiguous regions of a common target polynucleotide, from (ii) unrelated clusters. The signal may, for instance, take the form of a detectable optical signal emanating from a defined and identifiable location, such as a fluorescent signal, or may be a detectable signal originating from any other detectable label as provided herein. The reference position of a signal generated from two or more clusters may be used to determine the actual physical position on the surface of two clusters that are related by way of being the sites for simultaneous sequence reads from different portions of a common target polynucleotide. As discussed in more detail below, the sequence information obtained from the clusters and the proximity of clusters can in turn be used to determine the location of the sequences from the clusters in a genome (or other original sequence) from which the clusters were derived.

Following amplification, the polynucleotide molecules can be sequenced. The sequencing is carried out by a variety of known methods, including, but not limited to, sequencing by ligation, sequencing by synthesis or sequencing by hybridization.

Sequencing by synthesis, for example, is a technique wherein nucleotides are added successively to a free 3' hydroxyl group, typically provided by annealing of an oligonucleotide primer (e.g., a sequencing primer), resulting in synthesis of a nucleic acid chain in the 5' to 3' direction. These and other sequencing reactions may be conducted on the herein described surfaces bearing nucleic acid clusters. The reactions comprise one or a plurality of sequencing steps, each step comprising determining the nucleotide incorporated into a nucleic acid chain and identifying the position of the incorporated nucleotide on the surface. The nucleotides incorporated into the nucleic acid chain may be described as sequencing nucleotides and may comprise one or more detectable labels. Suitable detectable labels, include, but are not limited to, protons, haptens, radionucleotides, enzymes, fluorescent labels, chemiluminescent labels, and/or chromogenic agents. One method for detecting fluorescently labeled nucleotides comprises using laser light of a wavelength specific for the labeled nucleotides, or the use of other suitable sources of illumination. The fluorescence from the label on the nucleotide may be detected by a CCD camera or other suitable detection means. Suitable instrumentation for recording images of clustered arrays is described in WO 07/123744, the contents of which are incorporated herein by reference herein in its entirety.

Optionally, cycle sequencing is accomplished by stepwise addition of reversible terminator nucleotides containing, for example, a cleavable or photobleachable dye label as described, for example, in U.S. Pat. Nos. 7,427,673; 7,414,116; WO 04/018497; WO 91/06678; WO 07/123744; and U.S. Pat. No. 7,057,026, the disclosures of which are incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Alternatively, pyrosequencing techniques may be employed. Pyrosequencing detects the release of inorganic pyrophosphate (PPi) as particular nucleotides are incorporated into the nascent strand (Ronaghi et al., (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos.

6,210,891; 6,258,568; and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

Additional exemplary sequencing-by-synthesis methods that can be used with the methods described herein include those described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010251, the disclosures of which are incorporated herein by reference in their entireties.

Alternatively, sequencing by ligation techniques are used. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Other suitable alternative techniques include, for example, fluorescent in situ sequencing (FISSEQ), and Massively Parallel Signature Sequencing (VIPSS).

In traditional paired end sequencing, two sequencing reads are obtained from the same polynucleotide molecule to obtain the sequences of two different portions of the polynucleotide molecule. The two different portions can be contiguous or noncontiguous. Since the different portions are never separated, it is known that the two different portions come from the same original or parent nucleic acid molecule (e.g., a chromosome). By way of an example, in traditional paired end sequencing on a solid surface, a cluster of polynucleotide molecules comprising two different portions will be read twice because each portion that is to be read is located on the same polynucleotide molecule. In contrast, in the provided methods, the two different portions on the ends of the polynucleotide molecules are separated (e.g., they may form separate clusters). Thus, a single read provides the sequence information for both portions at the same time. The methods described herein provide clusters that tend to be spatially correlated. This is accomplished by using molecules sufficiently long such that the two ends of the molecule are captured on a surface in such a way that they are sufficiently separated from one another so that they can be differentiated optically, e.g., by the formation of two distinct clusters. The knowledge of the sequences of the polynucleotide molecules located on the surface of a support (e.g., in clusters) and the locations or relative proximities of the polynucleotide molecules can be used to determine or assemble the sequence of a target polynucleotide molecule (e.g., a gene, chromosome, chromosomal region, genome and the like). As described above, in the provided methods, sequences of a plurality of first and second portions are compared to the relative proximities of the first and second locations comprising the first and second portions, respectively, to determine the which first and second portions are paired and to determine the sequence of a plurality of polynucleotide molecules. The distance between the first and second locations (or first and second clusters) is correlated with the probability that the first and second locations or clusters are from the same target polynucleotide molecule (e.g., fragment). Optionally, the sequence and proximity of a polynucleotide molecule in a first location or cluster is compared to the sequence and proximity of a polynucleotide molecule in a second location or cluster. Optionally, the first and second portions comprise an oligonucleotide indexing tag. In other words, a "first" polynucleotide molecule comprising a first and second portion will comprise the same oligonucleotide indexing tag and a "second" different polynucleotide molecule comprising a first and second portion will comprise the same indexing tag. However, the tag for the first polynucleotide molecule is different from the tag for the second polynucleotide molecule. Since the first and second portions are located in different locations, the tag can be used to determine which first portion pairs with which second portion. This information can be used to determine the sequence of a target polynucleotide molecule (e.g., a chromosome) or a plurality of target polynucleotide molecules (e.g., a genome).

Although some aspects of the methods have been described above in a way to distinguish them from standard paired end sequencing, it will be understood that standard paired end sequencing techniques can be used in combination with other techniques and methods set forth herein. Specifically, paired end sequencing techniques can be used to determine the sequence of polynucleotides within individual, respective clusters on a surface and proximity between those clusters on the surface can be used to determine the sequence of the target polynucleotide from which the clusters were derived. Methods for carrying out paired end sequencing that can be useful in the methods set forth herein are described in the art, for example, in Bentley et al., Nature, 456:53-58 (2008); WO 07/010252; WO 07/091077; WO 08/041002 and WO 09/032167, which are incorporated by reference herein in their entireties.

The provided methods can be used for de novo sequencing or re-sequencing. In the context of re-sequencing, the sequences of the first and second portions are compared to a reference sequence. Information about the physical proximity of clusters on the surface of a flow cell or other substrate can be used to further confirm that two clusters or two locations contain noncontiguous sequences that were derived from a single fragment that was seeded onto the surface as opposed to being unlinked sequences (i.e., sequences not located on the same original or parent target polynucleotide molecule).

Once the reads from each cluster or location are obtained, algorithms are used to re-assemble the data. For an example of paired-end read alignments and assembly see, e.g., Batzoglou et al. (2002) Genome Res., 12(1):177-189. Sequence information from each individual cluster or location is obtained and the clusters or locations are paired together based on their proximity on the surface. In one embodiment, the shorter the distance between clusters indicates that the clusters comprise polynucleotide molecules of noncontiguous or contiguous sequences from the same parent or target polynucleotide molecule. The distance between clusters can be correlated with the probability that the clusters are from the same target polynucleotide molecule or the same fragment of the target polynucleotide molecule based on the length of the original polynucleotide molecule hybridized to the surface. Two clusters arising from the ends of each strand are separated on the surface by the physical length that is the same or less than the length of the initial fragments (approximately). In other words, the center-center distance between two clusters from the opposite ends of a single polynucleotide molecule is approximately no longer than the length of the polynucleotide molecule used to generate the clusters. Similarly, the distance between two locations to which first and second portions of polynucleotide molecules are bound is no longer than the length of the polynucleotide molecule. Nucleic acid fragment sizes for double stranded duplexes correspond to 0.34 nm per base pair. Thus, the ends of a 10 kB double stranded fragment should be approximately 3.4 micrometers apart or less, and a 100 kB fragment should be approximately 34 micrometers apart or less. For clusters that average around 1 micron, two clusters originating from the ends of long fragments will appear close to each other on the surface.

Whether locations or clusters, using the known length of the starting fragments within a range of sizes, it is possible to work out the maximum separation possible for the two ends of each fragment. Pairing together all the sequences of the clusters or locations within a known proximity on the surface gives a finite number of possible paired sequences for a particular fragment size. This can be carried out until the entire sequence of the target polynucleotide molecule (e.g., chromosome fragments) or plurality of target polynucleotide molecules (e.g., genome) is assembled. Depending on the complexity of the sample, it should be possible to discount the majority of the sequences as coming from clearly different molecules (e.g., different chromosome fragments). For example, in the case of a human genomic DNA sample, if there are 6 individual sequences within a small area of surface, two from one chromosome fragment, two from another chromosome fragment, and two from a third chromosome fragment, it is straightforward to pair the sequences together. Similarly, if one of the six sequences is ambiguous for two locations in the human genome, the identity of the other 5 sequences (2 correlated pairs and one unambiguous sequence) can be used to assist in determining where the ambiguous sequence lies in the genome.

As discussed above, indexing tags can also be used to assist in assembling the sequence of a target polynucleotide molecule (e.g., chromosome fragments) or plurality of target polynucleotide molecules (e.g., genome). By way of example, target polynucleotide molecule(s) can be fragmented and adapters comprising indexing tags can be attached to the ends of the fragment. The fragment, thus, contains first and second portions that, when separated, have the same indexing tag.

Another embodiment that can be used in conjunction with all other embodiments described herein includes fragmenting the target polynucleotide molecule with a restriction enzyme to generate non-random ends. This can be used to help determine the true ends of the fragment based on the knowledge that the end of the fragment will be the sequence of the restriction enzyme site.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation may not be explicitly disclosed, each is specifically contemplated and described herein. For example, if a method is disclosed and discussed and a number of modifications that can be made to the method steps are discussed, each and every combination and permutation of the method steps, and the modifications that are possible are specifically contemplated unless specifically indicated to the contrary. Likewise, any subset or combination of these is also specifically contemplated and disclosed. This concept applies to all aspects of this disclosure. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

EXAMPLES

Example 1. Obtaining Paired-End Information from a Long DNA Fragment

With reference to FIG. 1, genomic DNA is fragmented into large fragments (i.e. 100 Kb or more). After end repair, adapters are then ligated onto the 3' ends (e.g., adapters can be SBS3' or SBS8'). The molecules are then flowed inside a flowcell that has been grafted with blocked P5 and P7 oligonucleotides and also a certain amount of unblocked P5-SBS3 (or P7-SBS8). Although FIG. 1-1 refers to a P5 oligo with reversible block 1 and P7 oligo with reversible block 2, it is noted that the blocks 1 and 2 on P5 and P7 can be the same block or different blocks. The ends of the genomic DNA molecule (SBS3' or SBS8') will hybridize to the reverse complement oligonucleotides present on the flowcell surface. In the next step, an extension with a dNTP mix that contains an optimal amount of dUTP (or other modified nucleotide that can be cleaved to form a 3' reversible block, such as a phosphate group) is performed. The modified nucleotide will be randomly incorporated into the growing DNA strand during the extension step and its concentration is optimized so that DNA molecules of an appropriate size range are generated. After extension, the modified nucleotides are cleaved and this leaves a reversible block onto the 3' end (i.e. phosphate). A modified nucleotide can be chosen such that is has a 3' reversible block and its incorporation causes termination of the extension reaction. The P5-SBS3 (or P7-SBS8) oligonucleotides that have not been hybridized and extended are then blocked (i.e. with ddNTPs). The reversible block at the 3' end of genomic DNA is now cleaved off and an adapter is ligated to the genomic DNA's 3' ends (either SBS8'-P7' or SBS3'-P5'). After removal of the 3' blocks from P5 and P7, amplification of the molecules and sequencing of the clusters is performed. The two ends of a molecule will tend to originate a pair of clusters that are spatially correlated. Thus, paired end information is obtained with a single read.

Example 2. Correlation Between Fragment Size and Cluster Distance

Figure 7:
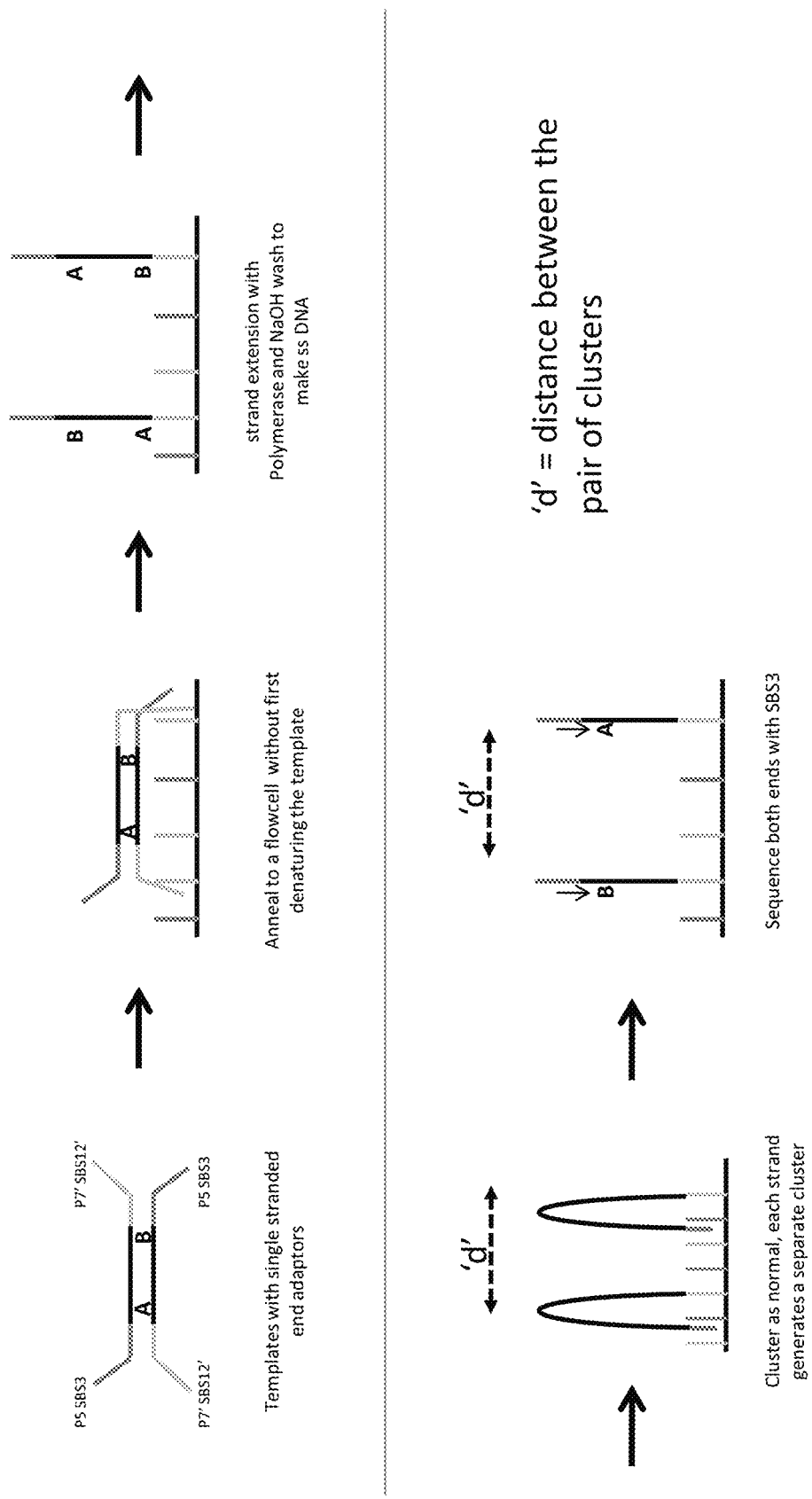
FIG. 7 is a schematic showing an exemplary method described herein. Double stranded fragments containing portions A and B to be sequenced are hybridized to oligos on a solid surface. The oligos are extended using the double stranded fragments as template to produce immobilized single stranded nucleic acid molecules. The immobilized single stranded nucleic acid molecules are amplified to produce clusters. The distance between clusters is denoted as 'd' and is correlated with the length of the double stranded fragment. The clusters are sequenced wherein the sequence of portion A is determined in one cluster and the sequence of portion B is determined in another cluster.

In order to determine paired end information in a single read, there needs to be a correlation between fragment size and the location of the paired portions on a surface. To determine whether there is a correlation between fragment size and the location of paired portions on a surface, two different sequencing methods were carried out as shown in the schematic of FIGS. 7 and 8. In FIG. 7, double stranded fragments containing portions A and B to be sequenced were hybridized to a surface. In FIG. 8, the double stranded fragments containing portions A and B were separated prior to hybridization to a surface. In both cases, each strand of the double stranded fragment was amplified to produce clusters. The clusters were sequenced wherein the sequence of portion A was determined in one cluster and the sequence of portion B was determined in another cluster. The results are shown in FIGS. 9A and 9B. FIGS. 9A and 9B are graphs showing the sequencing of an *E. coli* library with an average fragment size of 150 base pairs. FIG. 9A shows that, when the double stranded fragments are separated prior to hybridization to the surface (as shown in FIG. 8), the distance between pairs of clusters is random. In contrast, FIG. 9B shows that, when portions A and B are separated after the double stranded fragments are hybridized to the surface (as shown in FIG. 7), a significant proportion of cluster pairs align against the genome at a distance that corresponds to the average insert size of the library used in this experiment. Thus, when a sequencing method is performed wherein portions A and B are separated after hybridization to a surface, polynucleotide molecules can be sequenced by comparing the relative proximities of the clusters of portions A and B to determine which portions are paired and the sequences of the paired portions can be used to determine the sequence of the polynucleotide molecules. Thus, the methods provided herein provide paired-end information in a single read. The provided methods simplify paired-end sequencing while still taking advantage of the knowledge that two sequences (i.e., the two portions of the fragments) are linked or paired and, thus, known to occur on a single duplex. This knowledge can facilitate, for example, the assembly of whole genome sequences.

A number of embodiments have been described. Nevertheless, it will be understood that various modifications may be made. Accordingly, other embodiments are within the scope of the following claims.

What is claimed is:

1. A method for determining sequences of polynucleotides that contain a first portion and a second portion from the same polynucleotide, comprising:
   (a) providing a plurality of nucleic acid clusters attached to a surface, wherein the plurality of nucleic acid clusters is obtained by:
      (i) providing a plurality of double-stranded polynucleotides attached to a surface, wherein a first portion on a first strand of each of the plurality of double-stranded polynucleotide molecules is attached to a first location of the surface and a second portion on a second strand of each of the plurality of double-stranded polynucleotide molecules is attached to a second location of the surface, wherein the first portion and the second portion are located at the opposite ends of two complementary strands of each of the plurality of double-stranded polynucleotide molecules, and wherein each of the plurality of double-stranded polynucleotide molecules has a known length and the first strand and the second strand are the two complementary strands of each of the plurality of double-stranded polynucleotide molecules;
      (ii) separating the first portion on the first strand of each of the plurality of double-stranded polynucleotide molecules from the second portion on the second strand of each of the plurality of double-stranded polynucleotide molecules by denaturing the two complementary strands of each of the plurality of double-stranded polynucleotide molecules, thereby generating a plurality of denatured single polynucleotide strands such that the first portion on the first strand of each of the plurality of denatured single polynucleotide strands is immobilized on the first location of the surface and the second portion on the second strand of each of the plurality of denatured single polynucleotide strands is immobilized on the second location of the surface; and
      (iii) amplifying the first portion on the first strand of each of the plurality of denatured single polynucleotide strands immobilized on the first location and amplifying the second portion on the second strand of each of the plurality of denatured single polynucleotide strands immobilized on the second location, thereby obtaining the plurality of nucleic acid clusters on the surface;
   (b) identifying the locations of the plurality of nucleic acid clusters on the surface using an imaging device, and determining the distance from one cluster of the plurality of nucleic acid clusters to another cluster of the plurality of nucleic acid clusters on the surface;
   (c) determining the sequences of the first portion and the second portion of the plurality of nucleic acid clusters; and
   (d) comparing the location of each of the plurality of nucleic acid clusters on the surface, wherein the distance from one of the plurality of nucleic acid clusters to another of the plurality of nucleic acid clusters determines the probability of whether the sequence of the first portion of the one of the plurality of double-stranded polynucleotide molecules and the sequence of the second portion of the one of the plurality of double-stranded polynucleotide molecules are located on the same target polynucleotide molecule, and determining the sequences of the polynucleotides that contain the first portion and the second portion from the same polynucleotide.

2. The method of claim 1, further comprising performing steps (i)-(iii).

3. The method of claim 1, wherein step (c) is performed prior to step (b).

4. The method of claim 1, wherein the known length is a known average length.

5. The method of claim 1, wherein the known length of each of the plurality of polynucleotides is within a range of sizes.

6. The method of claim 1, wherein the first portion and second portion are noncontiguous.

7. The method of claim 1, wherein the surface is a patterned surface comprising a first population of oligonucleotides and a second population of oligonucleotides.

8. The method of claim 1, wherein step (c) is carried out by sequencing by ligation, sequencing by synthesis or sequencing by hybridization.

9. The method of claim 1, further comprising comparing the sequences of the first portion and second portion to a reference sequence.

10. The method of claim 1, wherein each of the plurality of double-stranded polynucleotide molecules comprises indexing tags.

11. The method of claim 10, wherein the first portion and second portion of each of the plurality of double-stranded polynucleotide molecules comprise the same tag from the indexing tags.

12. The method of claim 11, wherein the first portion and second portion of each of the plurality of double-stranded polynucleotide molecules retain said same tag after step (ii).

13. The method of claim 1, wherein the surface is a surface of a flow cell.

14. The method of claim 1, wherein step (i) comprises: producing fragments by fragmenting a genomic DNA, adding adaptors to the ends of the fragments, thereby obtaining the plurality of double-stranded polynucleotides.

* * * * *